(12) United States Patent
Lyman et al.

(10) Patent No.: US 6,919,206 B2
(45) Date of Patent: Jul. 19, 2005

(54) MEDIUM CONTAINING FLT3 LIGAND FOR CULTURING HEMATOPHOIETIC CELLS

(75) Inventors: Stewart D. Lyman, Seattle, WA (US); M. Patricia Beckmann, Poulsbo, WA (US)

(73) Assignee: Immunex Corporation, Thousand Oaks, CA (US)

( * ) Notice: Subject to any disclaimer, the term of this patent is extended or adjusted under 35 U.S.C. 154(b) by 0 days.

(21) Appl. No.: 08/994,468

(22) Filed: Dec. 19, 1997

(65) Prior Publication Data

US 2003/0148516 A1 Aug. 7, 2003

Related U.S. Application Data

(63) Continuation of application No. 08/444,627, filed on May 19, 1995, now abandoned, which is a division of application No. 08/243,545, filed on May 11, 1994, now Pat. No. 5,554,512, which is a continuation-in-part of application No. 08/209,502, filed on Mar. 7, 1994, now abandoned.

(51) Int. Cl.[7] .......................... A01N 1/00; A61K 38/18; A61K 38/19
(52) U.S. Cl. .......................... 435/386; 435/2; 435/375; 435/377; 435/383; 435/384; 435/385; 435/404; 435/405; 530/351; 424/85.2
(58) Field of Search .......................... 435/2, 404, 383, 435/386, 384, 372, 240.3, 375, 377, 405, 406, 325; 530/351, 350, 399; 424/85.2

(56) References Cited

U.S. PATENT DOCUMENTS

| | | | | |
|---|---|---|---|---|
| 5,061,620 A | * | 10/1991 | Tsukamoto et al. | 435/7.21 |
| 5,192,553 A | | 3/1993 | Boyse et al. | 424/529 |
| 5,199,942 A | | 4/1993 | Gillis | 604/4 |
| 5,326,558 A | | 7/1994 | Turner et al. | 424/85.1 |
| 5,635,386 A | * | 6/1997 | Palsson et al. | 435/372 |
| 5,843,423 A | * | 12/1998 | Lyman et al. | 424/85.1 |

FOREIGN PATENT DOCUMENTS

| | | | |
|---|---|---|---|
| EP | 627487 | | 5/1994 |
| WO | 9218615 | * | 10/1992 |
| WO | 9308268 | * | 4/1993 |

OTHER PUBLICATIONS

1. Attwood Science 290: 471–473 (2000).*
2. Metzler et al. Nature Struct. Biol. 4: 527–531, (1997).*
1. Skolnick et al. Trends Biotech 18: 34–39 (2000).*
2. Ngo et al. in the Protein Folding Problem and Tertiary Structure Prediction, 1994, Merz et al. (Ed.) Birkhauser, Boston, MA pp 433, 492–495.*

Ngo et al., Computational Complexity Protein Structure Prediction, and the Levintahal Paradox, 1994, Birkhauser Boston, vol. 14, pp. 491–495.*

Rudinger et al., Characteristics of the amino acids as components of a peptide hormone sequence, 1976, Peptide Hormons, pp. 1–7.*

Lardon et al., Exp. Hematol., 22:903–908, 1994.*

Lyman et al., Cell, 75:1157–1167, 1993.*

Brugger, W. et al., "Ex vivo expansion of enriched peripheral blood CD34+progenitor cells by stem cell factor, interleukin–1β (IL–1 β), IL–6, IL–3, interferon–γ, and erythropoietin," Blood, 81(10):2579–2584, 1993.

Culver, K. et al., "Lymphocytes as cellular vehicles for gene therapy in mouse and man," Proc. natl. Acad. Sci. USA, 88:3155–3159, 1991.

Durand, B. et al., "Long–term generation of colony–forming cells (CFC) from CD34+human umbilical cord blood cells," Leukemia and Lymphoma, 11 :263–273, 1993.

Lyman, S. et al., "Molecular cloning of a ligand for the flt3/flt–2 tyrosine kinase receptor: A proliferative factor for primitive hematopoietic cells," Cell, 75 :1157–1167, 1993.

Palsson, B. et al., "Expansion of human bone marrow progenitor cells in a high cell density continuous perfusion system," Biotechnology, 11 :365–372, 1993.

Stewart et al., "Post –5–Fluorouracil Human Marrow: Stem Cell Characteristics and Renewal Properties After Autologous Marrow Transplantation," Blood 81 :2283 (1993).

* cited by examiner

Primary Examiner—Phillip Gambel
(74) Attorney, Agent, or Firm—James E. Klaniecki

(57) ABSTRACT

Ligands for flt3 receptors capable of transducing self-renewal signals to regulate the growth, proliferation or differentiation of progenitor cells and stem cells are disclosed. The invention is directed to flt3-L as an isolated protein, the DNA encoding the flt3-L, host cells transfected with cDNAs encoding flt3-L, compositions comprising flt3-L, methods of improving gene transfer to a mammal using flt3-L, and methods of improving transplantations using flt3-L. Flt3 -L finds use in treating patients with anemia, AIDS and various cancers.

16 Claims, No Drawings

MEDIUM CONTAINING FLT3 LIGAND FOR CULTURING HEMATOHOIETIC CELLS

CROSS-REFERENCE TO RELATED APPLICATIONS

This application is a continuation of U.S. application Ser. No.08/444,627, filed May 19, 1995, now abandoned, which is a divisional of U.S. application Ser. No 08/243,545 filed May 11, 1994, now allowed and issued as U.S. Pat. No. 5,554,512, which is a continuation-in-part of U.S. application Ser. No. 08/209,502 filed Mar. 7, 1994, now abandoned.

FIELD OF THE INVENTION

The present invention relates to mammalian flt3-ligands, the nucleic acids encoding such ligands, processes for production of recombinant flt3-ligands, pharmaceutical compositions containing such ligands, and their use in various therapies.

BACKGROUND OF THE INVENTION

Blood cells originate from hematopoietic stem cells that become committed to differentiate along certain lineages, i.e., erythroid, megakaryocytic, granulocytic, monocytic, and lymphocytic. Cytokines that stimulate the proliferation and maturation of cell precursors are called colony stimulating factors ("CSFs"). Several CSFs are produced by T-lymphocytes, including interleukin-3 ("IL-3"), granulocyte-monocyte CSF (GM-CSF), granulocyte CSF (G-CSF), and monocyte CSF (M-CSF). These CSFs affect both mature cells and stem cells. Heretofore no factors have been discovered that are able to predominantly affect stem cells.

Tyrosine kinase receptors ("TKRs") are growth factor receptors that regulate the proliferation and differentiation of a number of cells (Yarden, Y. & Ullrich, A. *Annu. Rev. Biochem.*, 57, 443–478, 1988; and Cadena, D. L. & Gill, G. N. *FASEB J.*, 6, 2332–2337, 1992). Certain TKRs function within the hematopoietic system. For example, signaling through the colony-stimulating factor type 1 ("CSF-1"), receptor c-fms regulates the survival, growth and differentiation of monocytes (Stanley et al., *J. Cell Biochem.*, 21, 151–159, 1983). Steel factor ("SF", also known as mast cell growth factor, stem cell factor or kit ligand), acting through c-kit, stimulates the proliferation of cells in both myeloid and lymphoid compartments.

Flt3 (Rosnet et al. *Oncogene*, 6, 1641–1650, 1991) and flk-2 (Matthews et al., *Cell*, 65, 1143–1152, 1991) are variant forms of a TKR that is related to the c-fms and c-kit receptors. The flk-2 gene product is expressed on hematopoietic and progenitor cells, while the flt3 gene product has a more general tissue distribution. The flt3 and flk-2 receptor proteins are similar in amino acid sequence and vary at two amino acid residues in the extracellular domain and diverge in a 31 amino acid segment located near the C-termini (Lyman et al., *Oncogene*, 8, 815–822, 1993).

Flt3-ligand ("flt3-L") has been found to regulate the growth and differentiation of progenitor and stem cells and is likely to possess clinical utility in treating hematopoietic disorders, in particular, aplastic anemia and myelodysplastic syndromes. Additionally, flt3-L will be useful in allogeneic, syngeneic or autologous bone marrow transplants in patients undergoing cytoreductive therapies, as well as cell expansion. Flt3-L will also be useful in gene therapy and progenitor and stem cell mobilization systems.

Cancer is treated with cytoreductive therapies that involve administration of ionizing radiation or chemical toxins that kill rapidly dividing cells. Side effects typically result from cytotoxic effects upon normal cells and can limit the use of cytoreductive therapies. A frequent side effect is myelosuppression, or damage to bone marrow cells that give rise to white and red blood cells and platelets. As a result of myelosuppression, patients develop cytopenia, or blood cell deficits, that increase risk of infection and bleeding disorders.

Cytopenias increase morbidity, mortality, and lead to under-dosing in cancer treatment. Many clinical investigators have manipulated cytoreductive therapy dosing regimens and schedules to increase dosing for cancer therapy, while limiting damage to bone marrow. One approach involves bone marrow or peripheral blood cell transplants in which bone marrow or circulating hematopoietic progenitor or stem cells are removed before cytoreductive therapy and then reinfused following therapy to restore hematopoietic function. U.S. Pat. No. 5,199,942, incorporated herein by reference, describes a method for using GM-CSF, IL-3, SF, GM-CSF/IL-3 fusion proteins, erythropoietin ("EPO") and combinations thereof in autologous transplantation regimens.

High-dose chemotherapy is therapeutically beneficial because it can produce an increased frequency of objective response in patients with metastatic cancers, particularly breast cancer, when compared to standard dose therapy. This can result in extended disease-free remission for some even poor-prognosis patients. Nevertheless, high-dose chemotherapy is toxic and many resulting clinical complications are related to infections, bleeding disorders and other effects associated with prolonged periods of myelosuppression.

Myelodysplastic syndromes are stem cell disorders characterized by impaired cellular maturation, progressive pancytopenia, and functional abnormalities of mature cells. They have also been characterized by variable degrees of cytopenia, ineffective erythropoiesis and myelopoiesis with bone marrow cells that are normal or increased in number and that have peculiar morphology. Bennett et. al. (*Br. J. Haematol.* 1982; 51:189–199) divided these disorders into five subtypes: refractory anemia, refractory anemia with ringed sideroblasts, refractory anemia with excess blasts, refractory anemia with excess blasts in transformation, and chronic myelomonocytic leukemia. Although a significant percentage of these patients develop acute leukemia, a majority die from infectious or hemorrhagic complications. Treatment of theses syndromes with retinoids, vitamin D, and cytarabine has not been successful. Most of the patients suffering from these syndromes are elderly and are not suitable candidates for bone marrow transplantation or aggressive antileukemic chemotherapy.

Aplastic anemia is another disease entity that is characterized by bone marrow failure and severe pancytopenia. Unlike myelodysplastic syndrome, the bone marrow is acellular or hypocellular in this disorder. Current treatments include bone marrow transplantation from a histocompatible donor or immunosuppressive treatment with antithymocyte globulin (ATG). Similarly to myelodysplastic syndrome, most patients suffering from this syndrome are elderly and are unsuitable for bone marrow transplantation or for aggressive antileukemic chemotherapy. Mortality in these patients is exceedingly high from infectious or hemorrhagic complications.

Anemia is common in patients with acquired immune deficiency syndrome (AIDS). The anemia is usually more severe in patients receiving zidovudine therapy. Many important retroviral agents, anti-infectives, and antineoplastics suppress erythropoiesis. Recombinant EPO has been shown to normalize the patient's hematocrit and hemaoglobin levels, however, usually very high doses are required. A growth factor that stimulates proliferation of the erythroid lineage could be used alone or in combination with EPO or other growth factors to treat such patients and reduce the number of transfusions required. A growth factor that could also increase the number of T cells would find particular use in treating AIDS patients.

SUMMARY OF THE INVENTION

The present invention pertains to biologically active flt3-ligand (flt3-L) as an isolated or homogeneous protein. In addition, the invention is directed to isolated DNAs encoding flt3-L and to expression vectors comprising a cDNA encoding flt3-L. Within the scope of this invention are host cells that have been transfected or transformed with expression vectors that comprise a cDNA encoding flt3-L, and processes for producing flt3-L by culturing such host cells under conditions conducive to expression of flt3-L.

Flt3-L can be used to prepare pharmaceutical compositions to be used in allogeneic, syngeneic or autologous transplantation methods. Pharmaceutical compo- sitions may comprise flt3-L alone or in combination with other growth factors, such as interleukins, colony stimulating factors, protein tyrosine kinases and cytokines.

The invention includes methods of using flt3-L compositions in gene therapy and in treatment of patients suffering from myelodysplastic syndrome, aplastic anemia, HIV infection (AIDS) and cancers, such as breast cancer, lymphoma, small cell lung cancer, multiple myeloma, neuroblastoma, acute leukemia, testicular tumors, and ovarian cancer.

The present invention also pertains to antibodies, and in particular monoclonal antibodies, that are immunoreactive with flt3-L. Fusion proteins comprising a soluble portion of flt3-L and the constant domain of an immunoglobulin protein are also embodied in the invention.

The present invention also is directed to the use of flt3-L in peripheral blood progenitor or stem cell transplanation procedures. Typically, peripheral blood progenitor cells or stem cells are removed from a patient prior to myelosuppressive cytoreductive therapy, and then readministered to the patient concurrent with or following cytoreductive therapy to counteract the myelosuppressive effects of such therapy. The present invention provides for the use of an effective amount of flt3-L in at least one of the following manners: (i) flt3-L is administered to the patient prior to collection of the progenitor or stem cells to increase or mobilize the numbers of such circulating cells; (ii) following collection of the patient's progenitor or stem cells, flt3-L is used to expand such cells ex vivo; and (iii) flt3-L is administered to the patient following transplantation of the collected progenitor or stem cells to facilitate engraftment thereof. The transplantation method of the invention can further comprise the use of an effective amount of a cytokine in sequential or concurrent combination with the flt3-L. Such cytokines include, but are not limited to interleukins ("IL") IL-1, IL-2, IL-3, IL-4, IL-5, IL-6, IL-7, IL-8, IL-9, IL-10, IL-11, IL-12, IL-13, IL-14 or IL-15, a CSF selected from the group consisting of G-CSF, GM-CSF, M-CSF, or GM-CSF/IL-3 fusions, or other growth factors such as CSF-1, SF, EPO, leukemia inhibitory factor ("LIF") or fibroblast growth factor ("FGF"). The flt3-L is also useful in the same way for syngeneic or allogeneic transplantations.

The invention further includes a progenitor or stem cell expansion media comprising cell growth media, autologous serum, and flt3-L alone or in combination with a cytokine from the group listed above.

The invention further includes the use of flt3-L to expand progenitor or stem cells collected from umbilical cord blood. The expansion may be performed with flt3-L alone or in sequential or concurrent combination with a cytokine from the group listed above.

The invention further includes the use of flt3-L in gene therapy. Flt3-L permits proliferation and culturing of the early hematopoietic progenitor or stem cells that are to be transfected with exogenous DNA for use in gene therapy. Alternatively, a cDNA encoding flt3-L may be transfected into cells in order to ultimately deliver its gene product to the targeted cell or tissue.

In addition, the invention includes the use of flt3-L to stimulate production of erythroid cells in vivo for the treatment of anemia. Such use comprises administering flt3-L to the patient in need of such erythroid cell stimulation in conjunction with or following cytoreductive therapy. The treatment can include co-administration of another growth factor selected from the cytokines from the group listed above. Preferred cytokines for use in this treatment include EPO, IL-3, G-CSF and GM-CSF. Such treatment is especially useful for AIDS patients, and preferably for AIDS patients receiving AZT therapy.

Since flt3-L stimulates the production of stem cells, other non-hematopoietic stem cells bearing flt3 receptors can be affected by the flt3-L of the invention. Flt3-L is useful in in vitro fertilization procedures and can be used in vivo in the treatment of infertility conditions. In the gut, the flt3 ligand is useful in treating intestinal damage resulting from irradiation or chemotherapy. The flt3-L can be also used to treat patients infected with the human immunodeficiency virus (HIV). Such treatment would encompass the administration of the flt3-L to stimulate in vivo production, as well as the ex vivo expansion, of T cells and erythroid cells. Such treatment can prevent the deficiency of T cells, in particular CD4-positive T cells, and may elevate the patient's immune reponse against the virus, thereby improving the quality of life of the patient. The flt3-L can be used to stimulate the stem cells that lead to the development of hair follicles, thereby promoting hair growth.

In addition, flt3-L can be bound to a solid phase matrix and used to affinity-purify or separate cells that express flt3 on their cell surface. The invention encompasses separating cells having the flt3 receptor on the surface thereof from a mixture of cells in solution, comprising contacting the cells in the mixture with a contacting surface having a flt3-binding molecule thereon, and separating the contacting surface and the solution. Once separated, the cells can be expanded ex vivo using flt3-L and administered to a patient.

DETAILED DESCRIPTION OF THE INVENTION

A cDNA encoding murine flt3-L has been isolated and is disclosed in SEQ ID NO:1. A cDNA encoding human flt3-L also has been isolated and is disclosed in SEQ ID NO:5. This discovery of cDNAs encoding murine and human flt3-L enables construction of expression vectors comprising cDNAs encoding flt3-L; host cells transfected or transformed with the expression vectors; biologically active murine and human flt3-L as homogeneous proteins; and antibodies immunoreactive with the murine and the human flt3-L.

Flt3-L is useful in the enhancement, stimulation, proliferation or growth of cells expressing the flt3 receptor, including non-hematopoietic cells. Since the flt3 receptor is found in the brain, placenta, and tissues of nervous and hematopoietic origin, and finds distribution in the testis, ovaries, lymph node, spleen, thymus and fetal liver, treatment of a variety of conditions associated with tissue damage thereof is possible. While not limited to such, particular uses of the flt3-L are described infra.

As used herein, the term "flt3-L" refers to a genus of polypeptides that bind and complex independently with flt3 receptor found on progenitor and stem cells. The term "flt3-L" encompasses proteins having the amino acid sequence 1 to 231 of SEQ ID NO:2 or the amino acid sequence 1 to 235 of SEQ ID NO:6, as well as those proteins having a high degree of similarity or a high degree of identity with the amino acid sequence 1 to 231 of SEQ ID NO:2 or the amino acid sequence 1 to 235 of SEQ ID NO:6, and which proteins are biologically active and bind the flt3 receptor. In addition, the term refers to biologically active gene products of the DNA of SEQ ID NO:1 or SEQ ID NO:5. Further encompassed by the term "flt3-L" are the membrane-bound proteins (which include an intracellular region, a membrane region, and an extracellular region), and soluble or truncated proteins which comprise primarily the extracellular portion of the protein, retain biological activity and are capable of being secreted. Specific examples of such soluble proteins are those comprising the sequence of amino acids 28–163 of SEQ ID NO:2 and amino acids 28–160 of SEQ ID NO:6.

The term "biologically active" as it refers to flt3-L, means that the flt3-L is capable of binding to flt3. Alternatively, "biologically active" means the flt3-L is capable of transducing a stimulatory signal to the cell through the membrane-bound flt3.

"Isolated" means that flt3-L is free of association with other proteins or polypeptides, for example, as a purification product of recombinant host cell culture or as a purified extract.

A "flt3-L variant" as referred to herein, means a polypeptide substantially homologous to native flt3-L, but which has an amino acid sequence different from that of native flt3-L (human, murine or other mammalian species) because of one or more deletions, insertions or substitutions. The variant amino acid sequence preferably is at least 80% identical to a native flt3-L amino acid sequence, most preferably at least 90% identical. The percent identity may be determined, for example, by comparing sequence information using the GAP computer program, version 6.0 described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353–358, 1979; (2) a penalty of 3.0 for each gap and an additional 0.10 penalty for each symbol in each gap; and (3) no penalty for end gaps. Variants may comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Naturally occurring flt3-L variants are also encompassed by the invention. Examples of such variants are proteins that result from alternate mRNA splicing events or from proteolytic cleavage of the flt3-L protein, wherein the flt3-L binding property is retained. Alternate splicing of MRNA may yield a truncated but biologically active flt3-L protein, such as a naturally occurring soluble form of the protein, for example. Variations attributable to proteolysis include, for example, differences in the N- or C-termini upon expression in different types of host cells, due to proteolytic removal of one or more terminal amino acids from the flt3-L protein (generally from 1–5 terminal amino acids).

The term "autologous transplantation" is described in U.S. Pat. No. 5,199,942, which is incorporated herein by reference. Briefly, the term means a method for conducting autologous hematopoietic progenitor or stem cell transplantation, comprising: (1) collecting hematopoietic progenitor cells or stem cells from a patient prior to cytoreductive therapy; (2) expanding the hematopoietic progenitor cells or stem cells ex vivo with flt3-L to provide a cellular preparation comprising increased numbers of hematopoietic progenitor cells or stem cells; and (3) administering the cellular preparation to the patient in conjunction with or following cytoreductive therapy. Progenitor and stem cells may be obtained from peripheral blood harvest or bone marrow explants. Optionally, one or more cytokines, selected from the group listed above can be combined with flt3-L to aid in the proliferation of particular hematopoietic cell types or affect the cellular function of the resulting proliferated hematopoietic cell population. Of the foregoing, SF, IL-1, IL-3, EPO, G-CSF, GM-CSF and GM-CSF/IL-3 fusions are preferred, with G-CSF, GM-CSF and GM-CSF/IL-3 fusions being especially preferred. The term "allogeneic transplantation" means a method in which bone marrow or peripheral blood progenitor cells or stem cells are removed from a mammal and administered to a different mammal of the same species. The term "syngeneic transplantation" means the bone marrow transplantation between gentically identical mammals.

The transplantation method of the invention described above optionally comprises a preliminary in vivo procedure comprising administering flt3-L alone or in sequential or concurrent combination with a recruitment growth factor to a patient to recruit the hematopoietic cells into peripheral blood prior to their harvest. Suitable recruitment factors are listed above, and preferred recruitment factors are flt3-L, SF, IL-1 and IL-3.

The method of the invention described above optionally comprises a subsequent in vivo procedure comprising administering flt3-L alone or in sequential or concurrent combination with an engraftment growth factor to a patient following transplantation of the cellular preparation to facilitate engraftment and augment proliferation of engrafted hematopoietic progenitor or stem cells from the cellular preparation. Suitable engraftment factors are listed above, and the preferred engraftment factors are GM-CSF, G-CSF, IL-3, IL-1, EPO and GM-CSF/IL-3 fusions.

The invention further includes a progenitor or stem cell expansion media comprising cell growth media, autologous serum, and flt3-L alone or in combination with a cytokine growth factor from the list above. Preferred growth factors are SF, GM-CSF, IL-3, IL-1, G-CSF, EPO, and GM-CSF/IL-3 fusions.

In particular, flt3-L can be used to stimulate the proliferation of hematopoietic and non-hematopoietic stem cells. Such stimulation is beneficial when specific tissue damage has occurred to these tissues. As such, flt3-L may be useful in treating neurological damage and may be a growth factor for nerve cells. It is probable that flt3-L would be useful in in vitro fertilization procedures and likely can be used in vivo in the treatment of infertility conditions. Flt3-L would be useful in treating intestinal damage resulting from irradiation or chemotherapy. Since the flt3 receptor is distributed on stem cells leading to the development of hair follicles, flt3-L would likely be useful to promote hair growth.

Since flt3-L has been shown to stimulate T cell proliferation as well as erythrocytes (see Examples, infra), flt3-L finds use in the treatment of patients infected with the human immunodeficiency virus (HIV). Such treatment would encompass the administration of flt3-L to stimulate in vivo production, as well as the ex vivo expansion, of T cells. In addition, flt3-L can prevent the deficiency of $CD4^+$ T cells. Such treatment may elevate or maintain a patient's immune reponse against the virus, thereby improving or maintaining a patient's quality of life. In addition, such in vivo treatment would stimulate cells of the erythroid lineage, thereby improving a patient's hematocrit and hemaglobin levels. Flt3-L can be administered in this setting alone or in sequential or concurrent combination with cytokines selected from the group listed above.

Flt3-L is useful in gene therapy due to its specificity for progenitor and stem cells. Gene therapy involves administration of exogenous DNA-transfected cells to a host that are allowed to engraft. See e.g., Boggs, *International J. Cell Cloning*, 8:80-96, (1990); Kohn et. al., *Cancer Invest.*, 7(2):179–192 (1989); Lehn, *Bone Marrow Transpl.*, 5:287–293 (1990); and Verma, *Scientific American*, pp. 68–84 (1990). Using gene therapy methods known in the art, a method of transferring a gene to a mammal comprises the steps of (a) culturing early hematopoietic cells in media comprising flt3-L alone or in sequential or concurrent combination with a cyokine selected from the group listed above; (b) transfecting the cultured cells from step (a) with the exogenous gene; and (c) administering the transfected cells to the mammal. Within this method is the novel method of transfecting progenitor or stem cells with a gene comprising the steps of: (a) and (b) above. Furthermore, using the same or simolar methods, the cDNA encoding the flt3-L can be transfected into such delivery cells to deliver the flt3-L gene product to the targetted tissue.

Example 1 describes the construction of a novel flt3:Fc fusion protein utilized in the screening for flt3-L. Other antibody Fc regions may be substituted for the human IgG1 Fc region described in Example 1. Other suitable Fc regions are those that can bind with high affinity to protein A or protein G, and include the Fc region of human IgG1 or fragments of the human or murine IgG1 Fc region, e.g., fragments comprising at least the hinge region so that interchain disulfide bonds will form. The flt3:Fc fusion protein offers the advantage of being easily purified. In addition, disulfide bonds form between the Fc regions of two separate fusion protein chains, creating dimers. The dimeric flt3:Fc receptor was chosen for the potential advantage of higher affinity binding of flt3-L, in view of the possibility that the ligand being sought would be multimeric.

As described supra., an aspect of the invention is soluble flt3-L polypeptides. Soluble flt3-L polypeptides comprise all or part of the extracellular domain of a native flt3-L but lack the transmembrane region that would cause retention of the polypeptide on a cell membrane. Soluble flt3-L polypeptides advantageously comprise the native (or a heterologous) signal peptide when initially synthesized to promote secretion, but the signal peptide is cleaved upon secretion of flt3-L from the cell. Soluble flt3-L polypeptides encompassed by the invention retain the ability to bind the flt3 receptor. Indeed, soluble flt3-L may also include part of the transmembrane region or part of the cytoplasmic domain or other sequences, provided that the soluble flt3-L protein can be secreted.

Soluble flt3-L may be identified (and distinguished from its non-soluble membrane-bound counterparts) by separating intact cells which express the desired protein from the culture medium, e.g., by centrifugation, and assaying the medium (supernatant) for the presence of the desired protein. The presence of flt3-L in the medium indicates that the protein was secreted from the cells and thus is a soluble form of the desired protein.

Soluble forms of flt3-L possess many advantages over the native bound flt3-L protein. Purification of the proteins from recombinant host cells is feasible, since the soluble proteins are secreted from the cells. Further, soluble proteins are generally more suitable for intravenous administration.

Examples of soluble flt3-L polypeptides include those comprising a substantial portion of the extracellular domain of a native flt3-L protein. Such soluble mammalian flt3-L proteins comprise amino acids 28 through 188 of SEQ ID NO: 2 or amino acids 28 through 182 of SEQ ID NO:6. In addition, truncated soluble flt3-L proteins comprising less than the entire extracellular domain are included in the invention. Such truncated soluble proteins are represented by the sequence of amino acids 28–163 of SEQ ID NO:2, and amino acids 28–160 of SEQ ID NO:6. When initially expressed within a host cell, soluble flt3-L may additionally comprise one of the heterologous signal peptides described below that is functional within the host cells employed. Alternatively, the protein may comprise the native signal peptide, such that the mammalian flt3-L comprises amino acids 1 through 188 of SEQ ID NO:2 or amino acids 1 through 182 of SEQ ID NO:6. In one embodiment of the invention, soluble flt3-L was expressed as a fusion protein comprising (from N- to C-terminus) the yeast α factor signal peptide, a FLAG® peptide described below and in U.S. Pat. No. 5,011,912, and soluble flt3-L consisting of amino acids 28 to 188 of SEQ ID NO:2. This recombinant fusion protein is expressed in and secreted from yeast cells. The FLAG® peptide facilitates purification of the protein, and subsequently may be cleaved from the soluble flt3-L using bovine mucosal enterokinase. Isolated DNA sequences encoding soluble flt3-L proteins are encompassed by the invention.

Truncated flt3-L, including soluble polypeptides, may be prepared by any of a number of conventional techniques. A desired DNA sequence may be chemically synthesized using techniques known per se. DNA fragments also may be produced by restriction endonuclease digestion of a full length cloned DNA sequence, and isolated by electrophoresis on agarose gels. Linkers containing restriction endonuclease cleavage site(s) may be employed to insert the desired DNA fragment into an expression vector, or the fragment may be digested at cleavage sites naturally present therein. The well known polymerase chain reaction procedure also may be employed to amplify a DNA sequence encoding a desired protein fragment. As a further alternative, known mutagenesis techniques may be employed to insert a stop codon at a desired point, e.g., immediately downstream of the codon for the last amino acid of the extracellular domain.

In another approach, enzymatic treatment (e.g., using Bal 31 exonuclease) may be employed to delete terminal nucleotides from a DNA fragment to obtain a fragment having a particular desired terminus. Among the commercially available linkers are those that can be ligated to the blunt ends produced by Bal 31 digestion, and which contain restriction endonuclease cleavage site(s). Alternatively, oligonucleotides that reconstruct the N- or C-terminus of a DNA fragment to a desired point may be synthesized and ligated to the DNA fragment. The synthesized oligonucleotide may contain a restriction endonuclease cleavage site upstream of the desired coding sequence and position an initiation codon (ATG) at the N-terminus of the coding sequence.

As stated above, the invention provides isolated or homogeneous flt3-L polypeptides, both recombinant and non-recombinant. Variants and derivatives of native flt3-L proteins that retain the desired biological activity (e.g., the ability to bind flt3) may be obtained by mutations of nucleotide sequences coding for native flt3-L polypeptides. Alterations of the native amino acid sequence may be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene wherein predetermined codons can be altered by substitution, deletion or insertion. Exemplary methods of making the alterations set forth above are disclosed by Walder et al. (*Gene* 42:133, 1986); Bauer et al. (*Gene* 37:73, 1985); Craik (*BioTechniques*, January 1985, 12–19); Smith et al. (*Genetic Engineering: Principles and Methods*, Plenum Press, 1981); Kunkel (*Proc. Natl. Acad. Sci. USA* 82:488, 1985); Kunkel et al. (*Methods in Enzymol.* 154:367, 1987); and U.S. Pat. Nos. 4,518,584 and 4,737,462 all of which are incorporated by reference.

Flt3-L may be modified to create flt3-L derivatives by forming covalent or aggregative conjugates with other chemical moieties, such as glycosyl groups, lipids, phosphate, acetyl groups and the like. Covalent derivatives of flt3-L may be prepared by linking the chemical moieties to functional groups on flt3-L amino acid side chains or at the N-terminus or C-terminus of a flt3-L polypeptide or the extracellular domain thereof. Other derivatives of flt3-L within the scope of this invention include covalent or aggregative conjugates of flt3-L or its fragments with other proteins or polypeptides, such as by synthesis in recombinant culture as N-terminal or C-terminal fusions. For example, the conjugate may comprise a signal or leader polypeptide sequence (e.g. the α-factor leader of *Saccharomyces*) at the N-terminus of a flt3-L polypeptide. The signal or leader peptide co-translationally or post-translationally directs transfer of the conjugate from its site of synthesis to a site inside or outside of the cell membrane or cell wall.

Flt3-L polypeptide fusions can comprise peptides added to facilitate purification and identification of flt3-L. Such peptides include, for example, poly-His or the antigenic identification peptides described in U.S. Pat. No. 5,011,912 and in Hopp et al., *Bio/Technology* 6:1204, 1988.

The invention further includes flt3-L polypeptides with or without associated native-pattern glycosylation. Flt3-L expressed in yeast or mammalian expression systems (e.g., COS-7 cells) may be similar to or significantly different from a native flt3-L polypeptide in molecular weight and glycosylation pattern, depending upon the choice of expression system. Expression of flt3-L polypeptides in bacterial expression systems, such as *E. coli*, provides non-glycosylated molecules.

Equivalent DNA constructs that encode various additions or substitutions of amino acid residues or sequences, or deletions of terminal or internal residues or sequences not needed for biological activity or binding are encompassed by the invention. For example, N-glycosylation sites in the flt3-L extracellular domain can be modified to preclude glycosylation, allowing expression of a reduced carbohydrate analog in mammalian and yeast expression systems. N-glycosylation sites in eukaryotic polypeptides are characterized by an amino acid triplet Asn-X-Y, wherein X is any amino acid except Pro and Y is Ser or Thr. The murine and human flt3-L proteins each comprise two such triplets, at amino acids 127–129 and 152–154 of SEQ ID NO:2, and at amino acids 126–128 and 150–152 of SEQ ID NO:6, respectively. Appropriate substitutions, additions or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Known procedures for inactivating N-glycosylation sites in proteins include those described in U.S. Pat. No. 5,071,972 and EP 276,846, hereby incorporated by reference.

In another example, sequences encoding Cys residues that are not essential for biological activity can be altered to cause the Cys residues to be deleted or replaced with other amino acids, preventing formation of incorrect intramolecular disulfide bridges upon renaturation. Other equivalents are prepared by modification of adjacent dibasic amino acid residues to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites. Both murine and human flt3-L contain two KEX2 protease processing sites at amino acids 216–217 and 217–218 of SEQ ID NO:2 and at amino acids 211–212 and 212–213 of SEQ ID NO:6, respectively.

Nucleic acid sequences within the scope of the invention include isolated DNA and RNA sequences that hybridize to the native flt3-L nucleotide sequences disclosed herein under conditions of moderate or severe stringency, and which encode biologically active flt3-L. Conditions of moderate stringency, as defined by Sambrook et al. *Molecular Cloning: A Laboratory Manual*, 2 ed. Vol. 1, pp. 1.101–104, Cold Spring Harbor Laboratory Press, (1989), include use of a prewashing solution of 5×SSC, 0.5% SDS, 1.0 mM EDTA (pH 8.0) and hybridization conditions of about 55° C., 5×SSC, overnight. Conditions of severe stringency include higher temperatures of hybridization and washing. The skilled artisan will recognize that the temperature and wash solution salt concentration may be adjusted as necessary according to factors such as the length of the probe.

Due to the known degeneracy of the genetic code wherein more than one codon can encode the same amino acid, a DNA sequence may vary from that shown in SEQ ID NO:1 and SEQ ID NO:5 and still encode an flt3-L protein having the amino acid sequence of SEQ ID NO:2 and SEQ ID NO:6, respectively. Such variant DNA sequences may result from silent mutations (e.g., occurring during PCR amplification), or may be the product of deliberate mutagenesis of a native sequence.

The invention provides equivalent isolated DNA sequences encoding biologically active flt3-L, selected from: (a) DNA derived from the coding region of a native mammalian flt3-L gene; (b) cDNA comprising the nucleotide sequence presented in SEQ ID NO:1 or SEQ ID NO:5; (c) DNA capable of hybridization to a DNA of (a) under moderately stringent conditions and which encodes biologically active flt3-L; and (d) DNA which is degenerate as a result of the genetic code to a DNA defined in (a), (b) or (c) and which encodes biologically active flt3-L. Flt3-L proteins encoded by such DNA equivalent sequences are encompassed by the invention.

DNA that are equivalents to the DNA sequence of SEQ ID NO:1 or SEQ ID NO:5, will hybridize under moderately stringent conditions to the native DNA sequence that encode polypeptides comprising amino acid sequences of 28–163 of SEQ ID NO:2 or 28–160 of SEQ ID NO:6. Examples of flt3-L proteins encoded by such DNA, include, but are not limited to, flt3-L fragments (soluble or membrane-bound) and flt3-L proteins comprising inactivated N-glycosylation site(s), inactivated KEX2 protease processing site(s), or conservative amino acid substitution(s), as described above. Flt3-L proteins encoded by DNA derived from other mammalian species, wherein the DNA will hybridize to the cDNA of SEQ ID NO:1 or SEQ ID NO:5, are also encompassed.

Variants possessing the requisite ability to bind flt3 receptor may be identified by any suitable assay. Biological activity of flt3-L may be determined, for example, by competition for binding to the ligand binding domain of flt3 receptor (i.e. competitive binding assays).

One type of a competitive binding assay for a flt3-L polypeptide uses a radiolabeled, soluble human flt3-L and intact cells expressing cell surface flt3 receptors. Instead of intact cells, one could substitute soluble flt3 receptors (such as a flt3:Fc fusion protein) bound to a solid phase through the interaction of a Protein A, Protein G or an antibody to the flt3 or Fc portions of the molecule, with the Fc region of the fusion protein. Another type of competitive binding assay utilizes radiolabeled soluble flt3 receptors such as a flt3:Fc fusion protein, and intact cells expressing flt3-L. Alternatively, soluble flt3-L could be bound to a solid phase to positively select flt3 expressing cells.

Competitive binding assays can be performed following conventional methodology. For example, radiolabeled flt3-L can be used to compete with a putative flt3-L homolog to assay for binding activity against surface-bound flt3 receptors. Qualitative results can be obtained by competitive autoradiographic plate binding assays, or Scatchard plots may be utilized to generate quantitative results.

Alternatively, flt3-binding proteins, such as flt3-L and anti-flt3 antibodies, can be bound to a solid phase such as a column chromatography matrix or a similar substrate suitable for identifying, separating or purifying cells that express the flt3 receptor on their surface. Binding of flt3-binding proteins to a solid phase contacting surface can be accomplished by any means, for example, by constructing a flt3-L:Fc fusion protein and binding such to the solid phase through the interaction of Protein A or Protein G. Various other means for fixing proteins to a solid phase are well known in the art and are suitable for use in the present invention. For example, magnetic microspheres can be coated with flt3-binding proteins and held in the incubation vessel through a magnetic field. Suspensions of cell mixtures containing hematopoietic progenitor or stem cells are contacted with the solid phase that has flt3-binding proteins thereon. Cells having the flt3 receptor on their surface bind to the fixed flt3-binding protein and unbound cells then are washed away. This affinity-binding method is useful for purifying, screening or separating such flt3-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner. In the case of flt3:flt3-L interactions, the enzyme preferably would cleave the flt3 receptor, thereby freeing the resulting cell suspension from the "foreign" flt3-L material. The purified cell population then may be expanded ex vivo prior to transplantation to a patient in an amount sufficient to reconstitute the patient's hematopoietic and immune system.

Alternatively, mixtures of cells suspected of containing flt3$^+$ cells first can be incubated with a biotinylated flt3-binding protein. Incubation periods are typically at least one hour in duration to ensure sufficient binding to flt3. The resulting mixture then is passed through a column packed with avidin-coated beads, whereby the high affinity of biotin for avidin provides the binding of the cell to the beads. Use of avidin-coated beads is known in the art. See Berenson, et al. *J. Cell. Biochem.*, 10D:239 (1986). Wash of unbound material and the release of the bound cells is performed using conventional methods.

In the methods described above, suitable flt3-binding proteins are flt3-L, anti-flt3 antibodies, and other proteins that are capable of high-affinity binding of flt3. A preferred flt3-binding protein is flt3-L.

As described above, flt3-L of the invention can be used to separate cells expressing flt3 receptors. In an alternative method, flt3-L or an extracellular domain or a fragment thereof can be conjugated to a detectable moiety such as $^{125}$I to detect flt3 expressing cells. Radiolabeling with $^{125}$I can be performed by any of several standard methodologies that yield a functional $^{125}$I-flt3-L molecule labeled to high specific activity. Or an iodinated or biotinylated antibody against the flt3 region or the Fc region of the molecule could be used. Another detectable moiety such as an enzyme that can catalyze a colorimetric or fluorometric reaction, biotin or avidin may be used. Cells to be tested for flt3 receptor expression can be contacted with labeled flt3-L. After incubation, unbound labeled flt3-L is removed and binding is measured using the detectable moiety.

The binding characteristics of flt3-L (including variants) may also be determined using the conjugated, soluble flt3 receptors (for example, $^{125}$I-flt3:Fc) in competition assays similar to those described above. In this case, however, intact cells expressing flt3 receptors, or soluble flt3 receptors bound to a solid substrate, are used to measure the extent to which a sample containing a putative flt3-L variant competes for binding with a conjugated a soluble flt3 to flt3-L.

Other means of assaying for flt3-L include the use of anti-flt3-L antibodies, cell lines that proliferate in response to flt3-L, or recombinant cell lines that express flt3 receptor and proliferate in the presenvce of flt3-L. For example, the BAF/BO3 cell line lacks the flt3 receptor and is IL-3 dependent. (See Hatakeyama, et al., *Cell,* 59:837–845 (1989)). BAF/BO3 cells transfected with an expression vector comprising the flt3 receptor gene proliferate in response to either IL-3 or flt3-L. An example of a suitable expression vector for transfection of flt3 is the pCAV/NOT plasmid, see Mosley et al., *Cell,* 59:335–348 (1989).

Flt3-L polypeptides may exist as oligomers, such as covalently-linked or non-covalently-linked dimers or trimers. Oligomers may be linked by disulfide bonds formed between cysteine residues on different flt3-L polypeptides. In one embodiment of the invention, a flt3-L dimer is created by fusing flt3-L to the Fc region of an antibody (e.g., IgG1) in a manner that does not interfere with binding of flt3-L to the flt3-ligand-binding domain. The Fc polypeptide preferably is fused to the C-terminus of a soluble flt3-L (comprising only the extracellular domain). General preparation of fusion proteins comprising heterologous polypeptides fused to various portions of antibody-derived polypeptides (including the Fc domain) has been described, e.g., by Ashkenazi et al. (*PNAS USA* 88:10535, 1991) and Byrn et al. (*Nature* 344:677, 1990), hereby incorporated by reference. A gene fusion encoding the flt3-L:Fc fusion protein is inserted into an appropriate expression vector. Flt3-L:Fc fusion proteins are allowed to assemble much like antibody molecules, whereupon interchain disulfide bonds form between Fc polypeptides, yielding divalent flt3-L. If fusion proteins are made with both heavy and light chains of an antibody, it is possible to form a flt3-L oligomer with as many as four flt3-L extracellular regions. Alternatively, one can link two soluble flt3-L domains with a peptide linker.

Recombinant expression vectors containing a DNA encoding flt3-L can be prepared using well known methods. The expression vectors include a flt3-L DNA sequence operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are "operably linked" when the regulatory sequence functionally relates to the flt3-L DNA sequence. Thus, a promoter nucleotide sequence is operably linked to a flt3-L DNA sequence if the promoter nucleotide sequence controls the transcription of the flt3-L DNA sequence. The ability to replicate in the desired host cells, usually conferred by an origin of replication, and a selection gene by which transformants are identified, may additionally be incorporated into the expression vector.

In addition, sequences encoding appropriate signal peptides that are not naturally associated with flt3-L can be incorporated into expression vectors. For example, a DNA sequence for a signal peptide (secretory leader) may be fused in-frame to the flt3-L sequence so that flt3-L is initially translated as a fusion protein comprising the signal peptide. A signal peptide that is functional in the intended host cells enhances extracellular secretion of the flt3-L polypeptide. The signal peptide may be cleaved from the flt3-L polypeptide upon secretion of flt3-L from the cell.

Suitable host cells for expression of flt3-L polypeptides include prokaryotes, yeast or higher eukaryotic cells. Appropriate cloning and expression vectors for use with bacterial, fungal, yeast, and mammalian cellular hosts are described, for example, in Pouwels et al. *Cloning Vectors: A Laboratory Manual,* Elsevier, N.Y., (1985). Cell-free translation systems could also be employed to produce flt3-L polypeptides using RNAs derived from DNA constructs disclosed herein.

Prokaryotes include gram negative or gram positive organisms, for example, *E. coli* or *Bacilli*. Suitable prokaryotic host cells for transformation include, for example, *E. coli, Bacillus subtilis, Salmonella typhimurium,* and various other species within the genera *Pseudomonas, Streptomyces,* and *Staphylococcus*. In a prokaryotic host cell, such as *E. coli,* a flt3-L polypeptide may include an N-terminal methionine residue to facilitate expression of the recombinant polypeptide in the prokaryotic host cell. The N-terminal Met may be cleaved from the expressed recombinant flt3-L polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. To construct en expression vector using pBR322, an appropriate promoter and a flt3-L DNA sequence are inserted into the pBR322 vector. Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776) and tac promoter (Maniatis, *Molecular Cloning: A Laboratory Manual,* Cold Spring Harbor Laboratory, p. 412, 1982). A particularly useful prokaryotic host cell expression system employs a phage λ $P_L$ promoter and a cI857ts thermolabile repressor sequence. Plasmid vectors available from the American Type Culture Collection which incorporate derivatives of the λ $P_L$ promoter include plasmid pHUB2 (resident in *E. coli* strain JMB9 (ATCC 37092)) and pPLc28 (resident in *E. coli* RR1 (ATCC 53082)).

Flt3-L polypeptides alternatively may be expressed in yeast host cells, preferably from the Saccharomyces genus (e.g., *S. cerevisiae*). Other genera of yeast, such as *Pichia*, *K. lactis* or *Kluyveromyces,* may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73,657 or in Fleer et. al., *Gene,* 107:285–195 (1991); and van den Berg et. al., *Bio/Technology,* 8:135–139 (1990). Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* may be constructed by inserting DNA sequences from pBR322 for selection and replication in *E. coli* (Amp$^r$ gene and origin of replication) into the above-described yeast vectors.

The yeast α-factor leader sequence may be employed to direct secretion of the flt3-L polypeptide. The α-factor leader sequence is often inserted between the promoter sequence and the structural gene sequence. See, e.g., Kurjan et al., *Cell* 30:933, 1982; Bitter et al., *Proc. Natl. Acad. Sci. USA* 81:5330, 1984; U.S. Pat. No. 4,546,082; and EP 324,274. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for Trp$^+$ transformants in a selective medium, wherein the selective medium consists of 0.67% yeast nitrogen base, 0.5% casamino acids, 2% glucose, 10 μg/ml adenine and 20 μg/ml uracil.

Yeast host cells transformed by vectors containing ADH2 promoter sequence may be grown for inducing expression in a "rich" medium. An example of a rich medium is one consisting of 1% yeast extract, 2% peptone, and 1% glucose supplemented with 80 μg/ml adenine and 80 μg/ml uracil. Derepression of the ADH2 promoter occurs when glucose is exhausted from the medium.

Mammalian or insect host cell culture systems could also be employed to express recombinant flt3-L polypeptides. Baculovirus systems for production of heterologous proteins in insect cells are reviewed by Luckow and Summers, *Bio/Technology* 6:47 (1988). Established cell lines of mammalian origin also may be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV-1/EBNA-1 cell line derived from the African green monkey kidney cell line CVI (ATCC CCL 70) as described by McMahan et al. (*EMBO J.* 10:2821, 1991).

Transcriptional and translational control sequences for mammalian host cell expression vectors may be excised from viral genomes. Commonly used promoter sequences and enhancer sequences are derived from Polyoma virus, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide other genetic elements for expression of a structural gene sequence in a mammalian host cell. Viral early and late promoters are particularly useful because both are easily obtained from a viral genome as a fragment which may also contain a viral origin of replication (Fiers et al., *Nature* 273:113, 1978). Smaller or larger SV40 fragments may also be used, provided the approximately 250 bp sequence extending from the Hind III site toward the Bgl I site located in the SV40 viral origin of replication site is included.

Exemplary expression vectors for use in mammalian host cells can be constructed as disclosed by Okayama and Berg (*Mol. Cell. Biol.* 3:280, 1983). A useful system for stable high level expression of mammalian cDNAs in C127 murine mammary epithelial cells can be constructed substantially as described by Cosman et al. (*Mol. Immunol.* 23:935, 1986). A useful high expression vector, PMLSV N1/N4, described by Cosman et al., *Nature* 312:768, 1984 has been deposited as ATCC 39890. Additional useful mammalian expression vectors are described in EP-A-0367566, and in U.S. Pat. application Ser. No. 07/701,415, filed May 16, 1991, incorporated by reference herein. The vectors may be derived from retroviruses. In place of the native signal sequence, a heterologous signal sequence may be added, such as the signal sequence for IL-7 described in U.S. Pat. No. 4,965,195; the signal sequence for IL-2 receptor described in Cosman et al., *Nature* 312:768 (1984); the IL-4 signal peptide described in EP 367,566; the type I IL-1 receptor signal peptide described in U.S. Pat. No. 4,968,607; and the type II IL-1 receptor signal peptide described in EP 460,846.

Flt3-L as an isolated or homogeneous protein according to the invention may be produced by recombinant expression systems as described above or purified from naturally occurring cells. Flt3-L can be purified to substantial homogeneity, as indicated by a single protein band upon analysis by SDS-polyacrylamide gel electrophoresis (SDS-PAGE).

One process for producing flt3-L comprises culturing a host cell transformed with an expression vector comprising a DNA sequence that encodes flt3-L under conditions sufficient to promote expression of flt3-L. Flt3-L is then recovered from culture medium or cell extracts, depending upon the expression system employed. As is known to the skilled artisan, procedures for purifying a recombinant protein will vary according to such factors as the type of host cells employed and whether or not the recombinant protein is secreted into the culture medium.

For example, when expression systems that secrete the recombinant protein are employed, the culture medium first may be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Finally, one or more reversed-phase high performance liquid chromatography (RP-HPLC) steps employing hydrophobic RP-HPLC media, (e.g., silica gel having pendant methyl or other aliphatic groups) can be employed to further purify flt3-L. Some or all of the foregoing purification steps, in various combinations, are well known and can be employed to provide a substantially homogeneous recombinant protein.

It is possible to utilize an affinity column comprising the ligand binding domain of flt3 receptors to affinity-purify expressed flt3-L polypeptides. Flt3-L polypeptides can be removed from an affinity column using conventional techniques, e.g., in a high salt elution buffer and then dialyzed into a lower salt buffer for use or by changing pH or other components depending on the affinity matrix utilized. Alternatively, the affinity column may comprise an antibody that binds flt3-L. Example 6 describes a procedure for employing flt3-L of the invention to generate monoclonal antibodies directed against flt3-L.

Recombinant protein produced in bacterial culture is usually isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

Transformed yeast host cells are preferably employed to express flt3-L as a secreted polypeptide in order to simplify purification. Secreted recombinant polypeptide from a yeast host cell fermentation can be purified by methods analogous to those disclosed by Urdal et al. (*J. Chromatog.* 296:171, 1984). Urdal et al. describe two sequential, reversed-phase HPLC steps for purification of recombinant human IL-2 on a preparative HPLC column.

Antisense or sense oligonucleotides comprising a single-stranded nucleic acid sequence (either RNA or DNA) capable of binding to a target flt3-L mRNA sequence (forming a duplex) or to the flt3-L sequence in the double-stranded DNA helix (forming a triple helix) can be made according to the invention. Antisense or sense oligonucleotides, according to the present invention, comprise a fragment of the coding region of flt3-L cDNA. Such a fragment generally comprises at least about 14 nucleotides, preferably from about 14 to about 30 nucleotides. The ability to create an antisense or a sense oligonucleotide, based upon a cDNA sequence for a given protein is described in, for example, Stein and Cohen, *Cancer Res.* 48:2659, 1988 and van der Krol et al., *BioTechniques* 6:958, 1988.

Binding of antisense or sense oligonucleotides to target nucleic acid sequences results in the formation of complexes that block translation (RNA) or transcription (DNA) by one of several means, including enhanced degradation of the duplexes, premature termination of transcription or translation, or by other means. The antisense oligonucleotides thus may be used to block expression of flt3-L proteins. Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences. Other examples of sense or antisense oligonucleotides include those oligonucleotides which are covalently linked to organic moieties, such as those described in WO 90/10448, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oliginucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. Antisense or sense oligonucleotides are preferably introduced into a cell containing the target nucleic acid sequence by insertion of the antisense or sense oligonucleotide into a suitable retroviral vector, then contacting the cell with the retrovirus vector containing the inserted sequence, either in vivo or ex vivo. Suitable retroviral vectors include, but are not limited to, the murine retrovirus M-MuLV, N2 (a retrovirus derived from M-MuLV), or or the double copy vectors designated DCT5A, DCT5B and DCT5C (see PCT Application US 90/02656).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Flt3-L polypeptides of the invention can be formulated according to known methods used to prepare pharmaceutically useful compositions. Flt3-L can be combined in admixture, either as the sole active material or with other known active materials, with pharmaceutically suitable diluents (e.g., Tris-HCl, acetate, phosphate), preservatives (e.g., Thimerosal, benzyl alcohol, parabens), emulsifiers, solubilizers, adjuvants and/or carriers. Suitable carriers and their formulations are described in Remington's Pharmaceutical Sciences, 16th ed. 1980, Mack Publishing Co. In addition, such compositions can contain flt3-L complexed with polyethylene glycol (PEG), metal ions, or incorporated into polymeric compounds such as polyacetic acid, polyglycolic acid, hydrogels, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance of flt3-L. Flt3-L can also be conjugated to antibodies against tissue-specific receptors, ligands or antigens, or coupled to ligands of tissue-specific receptors. Where the flt3 receptor is found on neoplastic cells, the flt3-L may be conjugated to a toxin whereby flt3-L is used to deliver the toxin to the specific site, or may be used to sensitize such neoplastic cells to subsequently administered anti-neoplastic agents.

Flt3-L can be administered topically, parenterally, or by inhalation. The term "parenteral" includes subcutaneous injections, intravenous, intramuscular, intracisternal injection, or infusion techniques. These compositions will typically contain an effective amount of the flt3-L, alone or in combination with an effective amount of any other active material. Such dosages and desired drug concentrations contained in the compositions may vary depending upon many factors, including the intended use, patient's body weight and age, and route of administration. Preliminary doses can be determined according to animal tests, and the scaling of dosages for human administration can be performed according to art-accepted practices. Keeping the above description in mind, typical dosages of flt3-L may range from about 10 μg per square meter to about 1000 μg per square meter. A preferred dose range is on the order of about 100 μg per square meter to about 300 μg per square meter.

In addition to the above, the following examples are provided to illustrate particular embodiments and not to limit the scope of the invention.

EXAMPLE 1

Preparation of Flt3-Receptor:Fc Fusion Protein

This example describes the cloning of murine flt3 cDNA, and the construction of an expression vector encoding a soluble murine flt3-receptor:Fc fusion protein for use in detecting cDNA clones encoding flt3-L. Polymerase chain reaction (PCR) cloning of the flt3 cDNA from a murine T-cell was accomplished using the oligonucleotide primers and the methods as described by Lyman et al., *Oncogene*, 8:815–822, (1993), incorporated herein by reference. The cDNA sequence and encoded amino acid sequence for mouse flt3 receptor is presented by Rosnet et el., *Oncogene*, 6:1641–1650, (1991), hereby incorporated by reference. The mouse flt3 protein has a 542 amino acid extracellular domain, a 21 amino acid transmembrane domain, and a 437 amino acid cytoplasmic domain.

Prior to fusing the murine flt3 cDNA to the N-terminus of cDNA encoding the Fc portion of a human IgG1 molecule, the amplified mouse flt3 cDNA fragment was inserted into Asp718-NotI site of pCAV/NOT, described in PCT Application WO 90/05183. DNA encoding a single chain polypeptide comprising the Fc region of a human IgG1 antibody was cloned into the SpeI site of the pBLUESCRIPT SK® vector, which is commercially available from Stratagene Cloning Systems, La Jolla, Calif. This plasmid vector is replicable in *E. coli* and contains a polylinker segment that includes 21 unique restriction sites. A unique BglII site was introduced near the 5' end of the inserted Fc encoding sequence, such that the BglII site encompasses the codons for amino acids three and four of the Fc polypeptide.

The encoded Fc polypeptide extends from the N-terminal hinge region to the native C-terminus, i.e., is an essentially full-length antibody Fc region. Fragments of Fc regions, e.g., those that are truncated at the C-terminal end, also may be employed. The fragments preferably contain multiple cysteine residues (at least the cysteine residues in the hinge reaction) to permit interchain disulfide bonds to form between the Fc polypeptide portions of two separate flt3:Fc fusion proteins, forming dimers as discussed above.

An Asp718 restriction endonuclease cleavage site was introduced upstream of the flt3 coding region. An Asp 718-NotI fragment of mouse flt3 cDNA (comprising the entire extracellular domain, the transmembrane region, and a small portion of the cytoplasmic domain) was isolated. The above-described Asp718-NotI flt3 partial cDNA was cloned into the pBLUESCRIPT SK® vector containing the Fc cDNA, such that the flt3 cDNA is positioned upstream of the Fc cDNA. Single stranded DNA derived from the resulting gene fusion was mutagenized by the method described in Kunkel (*Proc. Natl. Acad. Sci. USA* 82:488, 1985) and Kunkel et al. (*Methods in Enzymol.* 154:367, 1987) in order to perfectly fuse the entire extracellular domain of flt3 to the Fc sequence. The mutagenized DNA was sequenced to confirm that the proper nucleotides had been removed (i.e., transmembrane region and partial cytoplasmic domain DNA was deleted) and that the flt3 and Fc sequences were in the same reading frame. The fusion cDNA was then excised and inserted into a mammalian expression vector designated sfHAV-EO 409 which was cut with SalI-NotI, and the SalI and Asp718 ends blunted. The sfHAV-EO vector (also known as pDC406) is described by McMahan et al. (*EMBO J.*, 10; No. 10:2821–2832 (1991)).

Flt3:Fc fusion proteins preferably are synthesized in recombinant mammalian cell culture. The flt3:Fc fusion-containing expression vector was transfected into CV-1 cells (ATCC CCL 70) and COS-7 cells (ATCC CRL 1651), both derived from monkey kidney. Flt3:Fc expression level was relatively low in both CV-1 and COS-7 cells. Thus, expression in 293 cells (transformed primary human embryonal kidney cells, ATCC CRL 1573) was attempted.

The 293 cells transfected with the sfHAV-EO/flt3:Fc vector were cultivated in roller bottles to allow transient expression of the fusion protein, which is secreted into the culture medium via the flt3 signal peptide. The fusion protein was purified on protein A Sepharose columns, eluted, and used to screen cells for the ability to bind flt3:Fc, as described in Examples 2 and 3.

EXAMPLE 2

Screening Cells for Flt3:Fc Binding

Approximately 100 different primary cells and cell lines falling into the following general categories: primary murine fetal brain cells, murine fetal liver cell lines, rat fetal brain cell lines, human lung carcinoma (fibroblastoid) cell lines, human and murine lymphoid and myeloid cell lines were assayed for flt3:Fc binding. Cell lines were incubated with flt3:Fc, followed by a biotinylated anti-human Fc antibody, followed by streptavidin-phycoerythrin (Becton Dickinson). The biotinylated antibody was purchased from Jackson Immunoresearch Laboratories. Streptavidin binds to the biotin molecule attached to the anti-human Fc antibody, which in turn binds to the Fc portion of the flt3:Fc fusion protein. Phycoerythrin is a fluorescent phycobiliprotein which serves as a detectable label. The level of fluorescence signal was measured for each cell type using a FACScan® flow cytometer (Becton Dickinson). The cell types deemed positive for flt3:Fc binding were identified.

EXAMPLE 3

Isolation and Cloning of Flt3 L cDNA from Murine T-Cell cDNA Library

A murine T-cell cDNA library of cell line P7B-0.3A4 was chosen as a possible source of flt3-L cDNA. P7B-0.3A4 is a murine T cell clone that is Thy1.2$^+$, CD4$^-$, CD8$^-$, TCRab$^\pm$, CD44$^+$. It was originally cloned at a cell density of 0.33 cells/well in the presence of rHuIL-7 and immobilized anti-CD3 MAb, and was grown in continuous culture for more than 1 year by passage once a week in medium containing 15 ng/ml rHuIL-7. The parent cell line was derived from lymph node cells of SJL/J mice immunized with 50 nmoles PLP$_{139-151}$ peptide and 100 μg *Mycobacterium tuberculosis* H37Ra in Incomplete Freund's Adjuvant. PLP is the proteolipid protein component of the myelin sheath of the central nervous system. The peptide composed of amino acids 139–151 has previously been shown to be the encephalogenic peptide in experimental autoimmune encephalomyelitis (EAE), a murine model for multiple sclerosis in SJL/J mice. (Touhy, V. K., Z. Lu, R. A. Sobel, R. A. Laursen and M. B. Lees; 1989. Identification of an encephalitogenic determinant of myelin proteolipid protein for SJL mice. *J. Immunol.* 142:1523.) After the initial culture in the presence of antigen, the parent cell line, designated PLP7, had been in continuous culture with rHuIL-7 (and without antigen) for more than 6 months prior to cloning.

P7B-0.3A4 proliferates only in response to very high concentrations of PLP$_{139-151}$ peptide in the presence of irradiated syngeneic splenocytes and is not encephalogenic or alloresponsive. This clone proliferates in response to immobilized anti-CD3 MAb, IL-2, and IL-7, but not IL-4.

Binding of flt3:Fc was observed on murine T-cells and human T-cells, and therefore a murine T-cell line was chosen (0.3A4) due to its ease of growth. A murine 0.3A4 cDNA library in sfHAV-EO was prepared as described in McMahan et al. (*EMBO J.*, 10; No:10; 2821–2832 1991). sfHAV-EO is a mammalian expression vector that also replicates in *E. coli*. sfHAV-EO contains origins of replication derived from SV40, Epstein-Barr virus and pBR322 and is a derivative of HAV-EO described by Dower et al., *J.Immunol.* 142:4314 (1989). sfHAV-EO differs from HAV-EO by the deletion of the intron present in the adenovirus 2 tripartite leader sequence in HAV-EO. Briefly, murine T-cell cDNA was cloned into the SalI site of sfHAV-EO by an adaptor method similar to that described by Haymerle et al (*Nucl. Acids Res.* 14:8615, 1986), using the following oligonucleotide adapter pair:

```
5' TCGACTGGAACGAGACGACCTGCT 3'    SEQ ID NO:3

3'     GACCTTGCTCTGCTGGACGA 5'    SEQ ID NO:4
```

Double-stranded, blunt-ended, random-primed cDNA was prepared from 0.3A4 poly (A)+ RNA essentially as described by Gubler and Hoffman, *Gene*, 25:263–269 (1983), using a Pharmacia DNA kit. The above adapters were added to the cDNA as described by Haymerle et al., Low molecular weight material was removed by passage over Sephacryl S-1000 at 65° C., and the cDNA was ligated into sfHAV-EO410, which had previously been cut with SalI and ligated to the same oligonucleotide pair. This vector is designated as sfHAV-EO410. DNA was electroporated (Dower et al., *Nucleic Acids Res.*, 16:6127–6145, (1988) into *E. coli* DH10B, and after one hour growth at 37° C., the transformed cells were frozen in one milliliter aliquots in SOC medium (Hanahan et al., *J. Mol. Biol.*, 166:557–580, (1983) containing 20% glycerol. One aliquot was titered to determine the number of ampcillin-resistant colonies. The resulting 0.3A4 library had 1.84 million clones.

*E. coli* strain DH10B cells transfected with the cDNA library in sfHAV-EO410 were plated to provide approximately 1600 colonies per plate. Colonies were scraped from each plate, pooled, and plasmid DNA prepared from each pool. The pooled DNA, representing about 1600 colonies, was then used to transfect a sub-confluent layer of CV-1/EBNA-1 cells using DEAE-dextran followed by chloroquine treatment, similar to that described by Luthman et al., *Nucl. Acids Res.* 11:1295, (1983) and McCutchan et al., *J. Natl. Cancer Inst.* 41:351, (1986). The CV-1/EBNA-1 cell line (ATCC CRL10478) constitutively expresses EBV nuclear antigen-1 driven from the CMV immediate-early enhancer/promoter. CV1-EBNA-1 was derived from the African Green Monkey kidney cell line CV-1 (ATCC CCL 70), as described by McMahan et al. (*EMBO J.* 10:2821, 1991).

In order to transfect the CV-1/EBNA-1 cells with the cDNA library, the cells were maintained in complete medium (Dulbecco's modified Eagle's media (DMEM) containing 10% (v/v) fetal calf serum (FCS), 50 U/ml penicillin, 50 U/ml streptomycin, 2 mM L-glutamine) and were plated at a density of about $2\times10^5$ cells/well on single-well chambered slides (Lab-Tek). Slides were pretreated with 1 mil human fibronectin (10 µg/ml in PBS) for 30 minutes followed by 1 wash with PBS. Media was removed from the adherent cell layer and replaced with 1.5 ml complete medium containing 66.6 µM chloroquine sulfate. Two-tenths nil of DNA solution (2 µg DNA, 0.5 mg/ml DEAE-dextran in complete medium containing chloroquine) was then added to the cells and incubated for 5 hours. Following the incubation, the media was removed and the cells shocked by addition of complete medium containing 10% DMSO for 2.5 to 20 minutes followed by replacement of the solution with fresh complete medium. The cells were cultured for 2 to 3 days to permit transient expression of the inserted sequences.

Transfected monolayers of CV-1/EBNA-1 cells were assayed for expression of flt3-L by slide autoradiography essentially as described by Gearing et al. (*EMBO J.* 8:3667, 1989). Transfected CV-1/EBNA-1 cells (adhered to chambered slides) were washed once with binding medium with nonfat dry milk (BM-NFDM) (RPMI medium 1640 containing 25 mg/ml bovine serum albumin (BSA), 2 mg/mil sodium azide, 20 mM HEPES, pH 7.2, and 50 mg/ml nonfat dry milk). Cells were then incubated with flt3:Fc in BM-NFDM (1 µg/ml) for 1 hour at room temperature. After incubation, the cell monolayers in the chambered slides were washed three times with BM-NFDM to remove unbound flt3:Fc fusion protein and then incubated with 40 ng/ml $^{125}$I-mouse anti-human Fc antibody (described below) (a 1:50 dilution) for 1 hour at room temperature. The cells were washed three times with BM-NFDM, followed by 2 washes with phosphate-buffered saline (PBS) to remove unbound $^{125}$I-mouse anti-human Fc antibody. The cells were fixed by incubating for 30 minutes at room temperature in 2.5% glutaraldehyde in PBS, pH 7.3, washed twice in PBS and air dried. The chamber slides containing the cells were exposed on a Phophorimager (Molecular Dynamics) overnight, then dipped in Kodak GTNB-2 photographic emulsion (6× dilution in water) and exposed in the dark for 3–5 days at 4° C. in a light proof box. The slides were then developed for approximately 4 minutes in Kodak D19 developer (40 g/500 ml water), rinsed in water and fixed in Agfa G433C fixer. The slides were individually examined with a microscope at 25–40× magnification and positive cells expressing flt3-L were identified by the presence of autoradiographic silver grains against a light background.

The mouse anti-human Fc antibody was obtained from Jackson Laboratories. This antibody showed minimal binding to Fc proteins bound to the Fcγ receptor. The antibody was labeled using the Chloramine T method. Briefly, a Sephadex G-25 column was prepared according to the manufacturer's instructions. The column was pretreated with 10 column volumes of PBS containing 1% bovine serum albumin to reduce nonspecific adsorption of antibody to the column and resin. Nonbound bovine serum albumin was then washed from the column with 5 volumes of PBS lacking bovine serum albumin. In a microfuge tube 10 µg of antibody (dissolved in 10 µl of PBS) was added to 50 µl of 50 mM sodium phosphate buffer (pH 7.2) 2.0 mCi of carrier-free Na$^{125}$I was added and the solution was mixed well. 15 µl of a freshly prepared solution of chloramine-T (2 mg/ml in 0.1 M sodium phosphate buffer (pH 7.2)) was then added and the mixture was incubated for 30 minutes at room temperature, and the mixture then was immediately applied to the column of Sephadex G-25. The radiolabelled antibody was then eluted from the column by collecting 100–150 µl fractions of eluate. Bovine serum albumin was added to the eluted fractions containing the radiolabeled antibody to a final concentration of 1%. Radioiodination yielded specific activities in the range of $5-10\times10^{15}$ cpm/nmol protein.

Using the slide autoradiography approach, the approximately 1,840,000 cDNAs were screened in pools of approximately 1,600 cDNAs until assay of one transfectant pool showed multiple cells clearly positive for flt3:Fc binding. This pool was then partitioned into pools of 500 and again screened by slide autoradiography and a positive pool was identified. This pool was partitioned into pools of 100 and again screened.

Individual colonies from this pool of 100 were screened until a clone (clone #6C) was identified which directed synthesis of a surface protein with detectable flt3:Fc binding activity. This clone was isolated, and its 0.88 kb cDNA insert was sequenced.

The nucleotide and encoded amino acid sequences of the coding region of the murine flt3-ligand cDNA of clone #6C are presented in SEQ ID NOS:1 and 2. The cDNA insert is 0.88 kb in length. The open-reading frame within this sequence could encode a protein of 231 amino acids. Thus, DNA and encoded amino acid sequences for the 231-amino acid open reading frame are presented in SEQ ID NOS:1 and 2. The protein of SEQ ID NO:2 is a type I transmembrane protein, with an N-terminal signal peptide (amino acids 1 to 27), an extracellular domain (amino acids 28–188) a transmembrane domain (amino acids 189–211) and a cytoplasmic domain (amino acids 212–231). The predicted molecular weight of the native protein following cleavage of the signal sequence is 23,164 daltons. The mature protein has an estimated pI of 9.372. There are 56 bp of 5' noncoding sequence and 126 bp of 3' non-coding sequence flanking the coding region, including the added cDNA adapters. The above-described cloning procedure also produced a murine flt3 ligand clone #5H, which is identical to the #6C clone beginning at nucleotide 49 and continuing through nucleotide 545 (corresponding to amino acid 163) of SEQ ID NO:1. The #5H clone completely differs from that point onward, and represents an alternate splicing construct.

The vector sfHAV-EO410 containing the flt3-L cDNA in E. coli DH10B cells was deposited with the American Type Culture Collection, Rockville, Md., USA (ATCC) on Apr. 20, 1993 and assigned accession number ATCC 69286. The deposit was made under the terms of the Budapest Treaty.

EXAMPLE 4

Cloning of cDNA Encoding Human Flt3-L

A cDNA encoding human flt3-L was cloned from a human clone 22 T cell λgt10 random primed cDNA library as described by Sims et al., PNAS, 86:8946–8950 (1989). The library was screened with a 413 bp Ple I fragment corresponding to the extracellular domain of the murine flt3-L (nucleotides 103–516 of SEQ ID NO:1). The fragment was random primed, hybridized overnight to the library filters at 55° C. in oligo prehybridization buffer. The fragment was then washed at 55° C. at 2×SSC/0.1% SDS for one hour, followed by 1×SSC/0.1% SDS for one hour and then by 0.5×SSC/0,1% SDS for one hour. The DNA from the positive phage plaques was extracted, and the inserts were amplified by PCR using oligonucleotides specific for the phage arms. The DNA then was sequenced, and the sequence for clone #9 is shown in SEQ ID NO:5. Additional human flt3-L cDNA was isolated from the same λgt10 random primed cDNA library as described above by screening the library with a fragment of the extracellular domain of the murine clone #5H cDNA comprising a cDNA sequence essentially corresponding to nucleotides 128–541 of SEQ ID NO:1.

Sequencing of the 988 bp cDNA clone #9 revealed an open reading frame of 705 bp surrounded by 29 bp of 5' non-coding sequence and 250 bp of 3' non-coding sequence. The 3' non-coding region did not contain a poly-A tail. There were no in-frame stop codons upstream of the initiator methionine. The open reading frame encodes a type I transmembrane protein of 235 amino acids as shown by amino acids 1–235 of SEQ ID NO:6. The protein has an N-terminal signal peptide of alternatively 26 or 27 amino acids. There exists a slightly greater probability that the N-terminal signal peptide is 26 amino acids in length than 27 amino acids in length. The signal peptide is followed by a 156 or a 155 amino acid extracellular domain (for signal peptides of 26 and 27 amino acids, respectively); a 23 amino acid transmembrane domain and a 30 amino acid cytoplasmic domain. Human flt3-L shares overall 72% amino acid identity and 78% amino acid similarity with murine flt3-L. The vector pBLUESCRIPT SK(−) containing the human flt3-L cDNA of clone #9 was deposited with the American Type Culture Collection, Rockville, Md., USA (ATCC) on Aug. 6, 1993 and assigned acession number ATCC 69382. The deposit was made under the terms of the Budapest Treaty.

EXAMPLE 5

Expression of Flt3-L in Yeast

For expression of soluble flt3-L in yeast, synthetic oligonucleotide primers were used to amplify via PCR (Mullis and Faloona, Meth. Enzymol. 155:335–350, 1987) the entire extracellular coding domain of flt3-L between the end of the signal peptide and the start of the transmembrane segment. The 5' primer (5'-AATTGGTACCTTTGGATAAAAGAGACTACAAG GACGACGATGACAAGACACCTGACTGTTACT TCAGCCAC-3') SEQ ID NO:7 encoded a portion of of the alpha factor leader and an antigenic octapeptide, the FLAG sequence fused in-frame with the predicted mature N-terminus of flt3-L. The 3' oligonucleotide (5'-ATATGGATCCCTACTGCCTGGGCCGAGGCTCT GGGAG-3') SEQ ID NO:8 created a termination codon following Gln-189, just at the putative transmembrane region. The PCR-generated DNA fragment was ligated into a yeast expression vector (for expression in K. lactis) that directs secretion of the recombinant product into the yeast medium (Fleer et. al., Gene, 107:285–195 (1991); and van den Berg et. al., Bio/Technology, 8:135–139 (1990)). The FLAG:flt3-L fusion protein was purified from yeast broth by affinity chromotography as previously described (Hopp et. al., Biotechnology, 6:1204–1210, 1988).

EXAMPLE 6

Monoclonal Antibodies to Flt3-L

This example illustrates a method for preparing monoclonal antibodies to flt3-L. Flt3-L is expressed in mammalian host cells such as COS-7 or CV- 1/EBNA-1 cells and purified using flt3:Fc affinity chromatography. Purified flt3-L, a fragment thereof such as the extracellular domain, synthetic peptides or cells that express flt3-L can be used to generate monoclonal antibodies against flt3-L using conventional techniques, for example, those techniques described in U.S. Pat. No. 4,411,993. Briefly, mice are immunized with flt3-L as an immunogen emulsified in complete Freund's adjuvant, and injected in amounts ranging from 10–100 μg subcutaneously or intraperitoneally. Ten to twelve days later, the immunized animals are boosted with additional flt3-L emulsified in incomplete Freund's adjuvant. Mice are periodically boosted thereafter on a weekly to bi-weekly immunization schedule. Serum samples are periodically taken by retro-orbital bleeding or tail-tip excision to test for flt3-L antibodies by dot blot assay, ELISA (Enzyme-Linked Immunosorbent Assay) or inhibition of flt3 binding.

Following detection of an appropriate antibody titer, positive animals are provided one last intravenous injection of flt3-L in saline. Three to four days later, the animals are sacrificed, spleen cells harvested, and spleen cells are fused to a murine myeloma cell line, e.g., NS1 or preferably P3x63Ag8.653 (ATCC CRL 1580). Fusions generate hybridoma cells, which are plated in multiple microtiter plates in a HAT (hypoxanthine, aminopterin and thymidine) selective medium to inhibit proliferation of non-fused cells, myeloma hybrids, and spleen cell hybrids.

The hybridoma cells are screened by ELISA for reactivity against purified flt3-L by adaptations of the techniques disclosed in Engvall et al.,*Immunochem.* 8:871, 1971 and in U.S. Pat. No. 4,703,004. A preferred screening technique is the antibody capture technique described in Beckmann et al., (*J. Immunol.* 144:4212, 1990) Positive hybridoma cells can be injected intraperitoneally into syngeneic BALB/c mice to produce ascites containing high concentrations of anti-flt3-L-L monoclonal antibodies. Alternatively, hybridoma cells can be grown in vitro in flasks or roller bottles by various techniques. Monoclonal antibodies produced in mouse ascites can be purified by ammonium sulfate precipitation, followed by gel exclusion chromatography. Alternatively, affinity chromatography based upon binding of antibody to protein A or protein G can also be used, as can affinity chromatography based upon binding to flt3-L.

EXAMPLE 7

Use of Flt3-L Alone and in Combination with IL-7 or IL-3

This example demonstrates the stimulation and proliferation of AA4.1$^+$ fetal liver cells by compositions containing flt3-L and IL-7; as well as the stimulation and proliferation of c-kit-positive (c-kit$^+$) cells by compositions containing flt3-L and IL-3.

AA4.1-positive (AA4.1$^+$) expressing cells were isolated from the livers of day 14 fetal C57BL/6 mice by cell panning in Optilux 100 mm plastic Petri dishes (Falcon No. 1001, Oxnard, Calif.). Plates were coated overnight at 4° C. in PBS plus 0.1% fetal bovine serum (FBS) containing 10 μg/ml AA4.1 antibody (McKearn et. al., *J. Immunol.*, 132:332–339, 1984) and then washed extensively with PBS plus 1% FBS prior to use. A single cell suspension of liver cells was added at 10$^7$ cells/dish in PBS plus 1% FBS and allowed to adhere to the plates for two hours at 4° C. The plates were then extensively washed, and the adhering cells were harvested by scraping for analysis or further use in the hematopoiesis assays described below. FACS analysis using AA4.1 antibody demonstrated a >95% AA4.1$^+$ cell population.

C-kit$^+$ pluripotent stem cells were purified from adult mouse bone marrow (de Vries et. al., *J. Exp. Med.*, 176:1503–1509, 1992; and Visser and de Vries, *Methods in Cell Biol.*, 1993, submitted). Low density cells (≦1.078 g/cm$^3$) positive for the lectin wheat germ agglutinin and negative for the antigens recognized by the B220 and 15-1.4.1 (Visser et. al., *Meth. in Cell Biol.*, 33:451–468, 1990) monoclonal antibodies, could be divided into subpopulations of cells that do and do not express c-kit by using biotinylated Steel factor. The c-kit$^+$ fraction has been shown to contain pluripotent hematopoietic stem cells (de Vries et. al., *Science* 255:989–991, 1992; Visser and de Vries, *Methods in Cell Biol.*, 1993, submitted; and Ware et. al., 1993, submitted).

AA4.1+ Fetal liver cells were cultured in recombinant IL-7 (U.S. Pat. No. 4,965,195) at 100 ng/ml and recombinant flt3-L at 250 ng/ml. Flt3-L was used in three different forms in the experiments: (1) as present on fixed, flt3-L-transfected CV1/EBNA cells; (2) as concentrated culture supernatants from these same flt3-L-transfected CV1/EBNA cells; and (3) as a purified and isolated polypeptide preparation from yeast supernatant as described in Example 5.

Hematopoiesis Assays

The proliferation of c-kit$^+$ stem cells, fetal liver AA4.1$^+$ cells was assayed in [3H]-thymidine incorporation assays as essentially described by deVries et. al., *J. Exp. Med.*, 173:1205–1211, 1991. Purified c-kit$^+$ stem cells were cultured at 37° C. in a fully humidified atmosphere of 6.5% $CO_2$ and 7% $O_2$ in air for 96 hours. Murine recombinant IL-3 was used at a final concentration of 100 ng/ml. Subsequently, the cells were pulsed with 2 μCi per well of [3H]-thymidine (81 Ci/mmol; Amersham Corp., Arlington Heights, Ill.) and incubated for an additional 24 hours. AA4.1$^+$ cells (approximately 20,000 cells/well) were incubated in IL-7, flt3-L and flt3-L +IL-7 for 48 hours, followed by [3H]-thymidine pulse of six hours. The results of flt3-L and IL-7 are shown in Table I, and results of flt3-L and IL-3 are shown in Table II.

TABLE 1

Effect of Flt3-L and IL-7 on Proliferation of AA4.1 + Fetal Liver Cells.

| | Factor | | | |
|---|---|---|---|---|
| | Control | flt3-L | IL-7 | flt3-L + IL-7 |
| [3H]-thymidine incorporation (CPM) | 100 | 1000 | 100 | 4200 |

The combination of flt3-L and IL-7 produced a response that was approximately four-fold greater than flt3-L alone and approximately 40-fold greater than IL-7 alone.

TABLE II

Effect of Flt3-L and IL-3 on Proliferation of C-kit + Cells.

| | Factor | | | |
|---|---|---|---|---|
| | Control (vector alone) | flt3-L | IL-3 | flt3-L + IL-3 |
| [3H]-thymidine incorporation (CPM) | 100 | 1800 | 3000 | 9100 |

Culture supernatant from CV1/EBNA cells transfected with flt3-L cDNA stimulated the proliferation of c-kit$^+$ stem cells approximately 18-fold greater than the culture supernatant of CV1/EBNA cells transfected with the expression vector alone. Addition of IL-3 to flt3-L containing supernatant showed a synergistic effect, with approximately twice the degree of proliferation observed than would be expected if the effects were additive.

EXAMPLE 8

Construction of Flt3-L:Fc Fusion Protein

This example describes a methof for constructing a fusion protein comprising an extracellular region of the flt3-L and the Fc domain of a human immunoglobulin. The methods are essentially the same as those described in Example 1 for construction of a flt3:Fc fusion protein.

Prior to fusing a flt3-L cDNA to the N-terminus of cDNA encoding the Fc portion of a human IgG1 molecule, the flt3-L cDNA fragment is inserted into Asp718-NotI site of pCAV/NOT, described in PCT Application WO 90/05183. DNA encoding a single chain polypeptide comprising the Fc region of a human IgG1 antibody is cloned into the SpeI site of the pBLUESCRIPT SK® vector, which is commercially available from Stratagene Cloning Systems, La Jolla, Calif. This plasmid vector is replicable in *E. coli* and contains a polylinker segment that includes 21 unique restriction sites. A unique BglII site is then introduced near the 5' end of the inserted Fc encoding sequence, such that the BglII site encompasses the codons for amino acids three and four of the Fc polypeptide.

The encoded Fc polypeptide extends from the N-terminal hinge region to the native C-terminus, i.e., is an essentially full-length antibody Fc region. Fragments of Fc regions, e.g., those that are truncated at the C-terminal end, also may be employed. The fragments preferably contain multiple cysteine residues (at least the cysteine residues in the hinge reaction) to permit interchain disulfide bonds to form between the Fc polypeptide portions of two separate flt3-L:Fc fusion proteins, forming dimers.

An Asp718-StuI partial cDNA of flt3-L in pCAV/NOT can be cloned into a Asp718-SpeI site of pBLUESCRIPT SK® vector containing the Fc cDNA, such that the flt3-L cDNA is positioned upstream of the Fc cDNA. The sequence of single stranded DNA derived from the resulting gene fusion can be affected by template-directed mutagensis described by Kunkel (*Proc. Natl. Acad. Sci. USA* 82:488, 1985) and Kunkel et al. (*Methods in Enzymol.* 154:367, 1987) in order to perfectly fuse the entire extracellular domain of flt3-L to the Fc sequence. The resulting DNA can then be sequenced to confirm that the proper nucleotides are removed (i.e., transmembrane region and partial cytoplasmic domain DNA are deleted) and that flt3-L and Fc sequences are in the same reading frame. The fusion cDNA is then excised and inserted using conventional methods into the mammalian expression vector pCAV/NOT which is cut with Asp 718-NotI.

Flt3-L:Fc fusion proteins preferably are synthesized in recombinant mammalian cell culture. The flt3-L:Fc fusion-containing expression vector is then transfected into CV-1 cells (ATCC CCL 70) or COS-7 cells (ATCC CRL 1651). Expression in 293 cells (transformed primary human embryonal kidney cells, ATCC CRL 1573) also is feasible.

The 293 cells transfected with the pCAV/NOT/flt3-L:Fc vector are cultivated in roller bottles to allow transient expression of the fusion protein, which is secreted into the culture medium via the flt3-L signal peptide. The fusion protein can be purified on protein A Sepharose columns.

EXAMPLE 9

Generation of Transgenic Mice That Overexpress Flt3-L

This example describes a procedure used to generate transgenic mice that overexpress flt3-L. Flt3-L-overexpressing transgenic mice were studied to determine the biological effects of overexpression. Mouse (B16/J) pronuclei were microinjected with flt3-L DNA according to the method described by Gordon et al., *Science* 214:1244–1246, (1981). In general, fertilized mouse eggs having visible pronuclei were first placed on an injection chamber and held in place with a small pipet. An injection pipet was then used to inject the gene encoding the flt3-L (clone #6C) into the pronuclei of the egg. Injected eggs were then either (i) transferred into the oviduct of a 0.5 day p.c. pseudopregnant female; (ii) cultured in vitro to the two-cell stage (overnight) and transferred into the oviduct of a 0.5 day p.c. pseudopregnant female; or (iii) cultured in vitro to the blastocyst stage and transferred into the uterus of a 2.5 day p.c. pseudopregnant female. Preferably, either of the first two options can be used since they avoid extended in vitro culture, and preferably, approximately 20–30 microinjected eggs should be transferred to avoid small litters.

EXAMPLE 10

Flt3-L Stimulates Proliferation of Erythroid Cells in the Spleen

This example describes the effect of flt3-L on the production of erythroid cells in the spleen of transgenic mice. Transgenic mice were generated according to the procedures of Example 10. The mice were sacrificed and each intact spleen was made into a single cell suspension. The suspended cells were spun and then resuspended in 10 nil of medium that contained PBS+1% fetal bovine serum. Cell counts were performed thereon using a hemocytometer. Each cell specimen was counted with Trypan Blue stain to obtain a total viable cell count per milliliter of medium according to the following formula: (RBC+WBC)/ml, wherein RBC is the red blood cell count and WBC means the white blood cell count. Each specimen then was counted with Turk's stain to obtain a total white blood cell count per milliliter of medium. The total red blood cell count per milliliter was calculated for each specimen by subtracting the total white blood cell count per milliliter from the total viable cell count per milliliter. The results are shown in the following Table III.

TABLE III

Erythroid Cell Proliferation in Flt3-L-Overexpressing Transgenic Mice Spleen

| Mouse | Total Viable Cell (million cells/ml) | Total White Cell (million cells/ml) | Total Red Blood Cell (million cells/ml) |
| --- | --- | --- | --- |
| Control 1 | 29.7 | 27 | 2.7 |
| Control 2 | 31 | 24.6 | 6.4 |
| Transgenic 1 | 44.7 | 25.6 | 19.1 |
| Transgenic 2 | 37.3 | 28.4 | 8.9 |

From the data of Table III, the white blood cell counts per milliliter were approximately the same as the control mice. However, the red blood cell counts from the spleens of the two transgenic mice were approximately two to three-fold greater than observed in the control mice. Flt3-L stimulates an increase in cells of the erythroid lineage, possibly through stimulation of erythroid proogenitor cells, through the stimulation of cells that produce erythropoietin, or by blocking a mechanism that inhibits erythropoiesis.

EXAMPLE 11

Flt3-L Stimulates Proliferation of T Cells and Early B Cells

Bone marrow from 9 week old transgenic mice generated according to Example 10 was screened for the presence of various T and B cell phenotype markers using antibodies that are immunoreactive with such markers. The following markers were investigated: the B220 marker, which is specific to the B cell lineage; surface IgM marker (sIgM), which is specific to mature B cells; the S7 (CD43) marker, which is an early B cell marker; the Stem Cell Antigen-1

(SCA-1) marker, which is a marker of activated T cells and B cells; CD4, which is a marker for helper T cells and some stem cells; and the Mac-1 marker, which is specific to macrophages, were screened using well known antibodies against such markers. The following Table IV shows the data obtained from screening the bone marrow. Two transgenic mice from the same litter were analyzed against a normal mouse from the same litter (control), and an unrelated normal mouse (control).

TABLE IV

Effect of flt3-L Overexpression in Transgenic Mice
Percentage of Positive Cells

| Marker | Unrelated Control | Littermate Control | Transgenic #1 | Transgenic #2 |
|---|---|---|---|---|
| B220 | 30.64 | 27.17 | 45.84 | 48.78 |
| sIgM | 3.54 | 2.41 | 1.94 | 1.14 |
| S7(CD43) | 54.43 | 45.44 | 46.11 | 50.59 |
| SCA-1 | 10.92 | 11.74 | 19.45 | 27.37 |
| CD4 | 6.94 | 8.72 | 12.21 | 14.05 |
| Mac-1 | 36.80 | 27.15 | 21.39 | 18.63 |

The above data indicate that flt3-L overexpression in mice leads to an increase in the number of B cells, as indicated by the increase B220$^+$ cells and SCA-1$^+$ cells. Analysis of B220$^+$ cells by FACS indicated an increase in proB cells (HSA$^-$, S7$^+$). The increase in CD4$^+$ cells indicated an approximate two-fold increase in T cells and stem cells. The decrease in cells having the sIgM marker indicated that flt3-L does not stimulate proliferation of mature B cells. These data indicate that flt3-L increases cells with a stem cell, T cell or an early B cell phenotype, and does not stimulate proliferation of mature B cells or macrophages.

EXAMPLE 12

Analysis of the Thymus From Flt3-L-Overexpressing Mice

This Example describes the analysis of the thymus from the transgenic mice generated according to the procedure of Example 10. Six adult mice, each approximately three months of age, were sacrificed. The thymus from each mouse was removed and a single cell suspension was made.

FACS analysis demonstrated that no total change in cell number occurred and that the mice showed no change in the ratios of maturing thymocytes using the markers: CD4 vs. CD8; CD3 vs. $\alpha\beta$TCR (T cell receptor); and CD3 vs. $\gamma\delta$TCR (T cell receptor). However, a change in the ratios of certain cell types within the CD4$^-$ and CD8$^-$ compartment (i.e., the earliest cells with respect to development; which represent approximately 2% to 3% of total thymus cells) occurred. Specifically, CD4$^-$ and CD8$^-$ cells in the thymus develop in three stages. Stage 1 represents cells having the Pgp-1$^{++}$, HSA$^+$ and IL-2 receptor-negative ("IL-2R$^-$") markers. After stage 1, thymic cells develop to stage 2 consisting of cells having Pgp-1$^+$, HSA$^{++}$, and IL-2R$^{++}$ markers, and then to stage 3, characterized by cells having Pgp-1$^{+/-}$, HSA$^{++}$, and IL-2R$^-$markers. Thymic cells in stage 2 of the transgenic mice were reduced by about 50%, while the population of cells in stage 3 was proportionately increased. These data suggest that flt3-L drives the thymic cells from stage 2 to stage 3 of development, indicating that flt3-L is active on early T cells.

EXAMPLE 13

Use of Flt3-L in Peripheral Stem Cell Transplantation

This Example describes a method for using flt3-L in autologous peripheral stem cell (PSC) or peripheral blood progenitor cell (PBPC) transplantation. Typically, PBPC and PSC transplantation is performed on patients whose bone marrow is unsuitable for collection due to, for example, marrow abnormality or malignant involvement.

Prior to cell collection, it may be desirable to mobilize or increase the numbers of circulating PBPC and PSC. Mobilization can improve PBPC and PSC collection, and is achievable through the intravenous administration of flt3-L to the patients prior to collection of such cells. Other growth factors such as CSF-1, GM-CSF, SF, G-CSF, EPO, IL-1, IL-2, IL-3, IL-4, IL-5, IL-6, IL-7, IL-8, IL-9, IL-10, IL-11, IL-12, IL-13, IL-14, IL-15, GM-CSF/IL-3 fusion proteins, LIF, FGF and combinations thereof, can be likewise administered in sequence, or in concurrent combination with flt3-L. Mobilized or non-mobilized PBPC and PSC are collected using apheresis procedures known in the art. See, for example, Bishop et al., *Blood*, vol. 83, No. 2, pp. 610–616 (1994). Briefly, PBPC and PSC are collected using conventional devices, for example, a Haemonetics Model V50 apheresis device (Haemonetics, Braintree, Mass.). Four-hour collections are performed typically no more than five times weekly until approximately 6.5×10$^8$ mononuclear cells (MNC)/kg patient are collected. Aliquots of collected PBPC and PSC are assayed for granulocyte-macrophage colony-forming unit (CFU-GM) content by diluting approximately 1:6 with Hank's balanced salt solution without calcium or magnesium (HBSS) and layering over lymphocyte separation medium (Organon Teknika, Durham, N.C.). Following centrifugation, MNC at the interface are collected, washed and resuspended in HBSS. One milliliter aliquots containing approximately 300,000 MNC, modified McCoy's 5A medium, 0.3% agar, 200 U/mL recombinant human GM-CSF, 200 u/mL recombinant human IL-3, and 200 u/mL recombinant human G-CSF are cultured at 37° C. in 5% CO$_2$ in fully humidified air for 14 days. Optionally, flt3-L or GM-CSF/IL-3 fusion molecules (PIXY 321) may be added to the cultures. These cultures are stained with Wright's stain, and CFU-GM colonies are scored using a dissecting microscope (Ward et al., *Exp. Hematol.*, 16:358 (1988). Alternatively, CFU-GM colonies can be assayed using the CD34/CD33 flow cytometry method of Siena et al., *Blood*, Vol. 77, No. 2, pp 400–409 (1991), or any other method known in the art.

CFU-GM containing cultures are frozen in a controlled rate freezer (e.g., Cryo-Med, Mt. Clemens, Mich.), then stored in the vapor phase of liquid nitrogen. Ten percent dimethylsulfoxide can be used as a cryoprotectant. After all collections from the patient have been made, CFU-GM containing cultures are thawed and pooled. The thawed cell collection either is reinfused intravenoulsy to the patient or expanded ex vivo prior to reinfusion. Ex vivo expansion of pooled cells can be performed using flt3-L as a growth factor either alone, sequentially or in concurrent combination with other cytokines listed above. Methods of such ex vivo expansion are well known in the art. The cells, either expanded or unexpanded, are reinfused intravenously to the patient. To facilitate engraftment of the transplanted cells, flt3-L is administered simultaneously with, or subsequent to, the reinfusion. Such administration of flt3-L is made alone, sequentially or in concurrent combination with other cytokines selected from the list above.

EXAMPLE 14

Purification of Hematopoietic Progenitor and Stem Cells Using Flt3-L

This Example describes a method for purifying hematopoietic progenitor cells and stem cells from a suspension containing a mixture of cells. Cells from bone marrow and peripheral blood are collected using conventional procedures. The cells are suspended in standard media and then centrifuged to remove red blood cells and neutrophils. Cells located at the interface between the two phases (also known in the art as the buffy coat) are withdrawn and resuspended. These cells are predominantly mononuclear and represent a substantial portion of the early hematopoietic progenitor and stem cells. The resulting cell suspension then is incubated with biotinylated flt3-L for a sufficient time to allow substantial flt3:flt3-L interaction. Typically, incubation times of at least one hour are sufficient. After incubation, the cell suspension is passed, under the force of gravity, through a column packed with avidin-coated beads. Such columns are well known in the art, see Berenson, et al., *J. Cell Biochem.*, 10D:239 (1986). The column is washed with a PBS solution to remove unbound material. Target cells can be released from the beads and from flt3-L using conventional methods.

What is claimed is:

1. A hematopoietic cell expansion medium, comprising a cell growth medium and:
   (a) a polypeptide comprising amino acids 28–160 of SEQ ID NO:6;
   (b) a polypeptide comprising a fragment of ammino acids 28–160 of SEQ ID NO:6, wherein the fragment binds flt3; and
   (c) a polypeptide that binds flt3 that is at least 90% identical to amino acids 28–60 of SEQ ID NO:6.

2. The hematopoietic cell expansion medium of claim 1, further comprising a cellular growth factor.

3. The hematopoietic cell expansion medium of claim 1, further comprising G-CSF.

4. The hematopoietic cell expansion medium of claim 1, further comprising GM-CSF.

5. The hematopoietic cell expansion medium of claim 1, further comprising SF.

6. The hematopoietic cell expansion mediwn of claim 1, further comprising EPO.

7. The hematopoietic cell expansion medium of claim 1, further comprising a GM-CSF/IL-3 fusion protein.

8. The hematopoietic cell expansion medium of claim 1, further comprising IL-6.

9. An in vitro method for expanding hematopoietic cells, the method comprising contacting the cells with:
   (a) a polypeptide comprising amino acids 28–160 of SEQ ID NO:6;
   (b) a polypeptide comprising a fragment of acids 28–160 of SEQ ID NO:6, wherein the fragment binds flt3; and
   (c) a polypeptide that binds flt3 that is at least 90% identical to amino acids 28–160 of SEQ ID NO:6 in an amount sufficient to cause hematopoietic cell expansion.

10. The method according to claim 9, further comprising contacting the cells with a cellular growth factor.

11. The method according to claim 9, further comprising contacting the cells with G-CSF.

12. The method according to claim 9, further comprising contacting the cells with GM-CSF.

13. The method according to claim 9, further comprising contacting the cells with SF.

14. The method according to claim 9, further comprising contacting the cells with EPO.

15. The method according to claim 9, further comprising contacting the cells with a GM-CSF/IL-3 fusion protein.

16. The method according to claim 9, further comprising contacting the cells with IL-6.

* * * * *

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
      (A) LENGTH: 879 base pairs
      (B) TYPE: nucleic acid
      (C) STRANDEDNESS: single
      (D) TOPOLOGY: linear (ii) MOLECULE TYPE: cDNA to mRNA (iii) HYPOTHETICAL: NO (iv) ANTI-SENSE: NO (ix) FEATURE:
      (A) NAME/KEY: misc_feature
      (B) LOCATION: 1..25

(ix) FEATURE:
      (A) NAME/KEY: misc_feature
      (B) LOCATION: 855..879

(ix) FEATURE:
      (A) NAME/KEY: CDS
      (B) LOCATION: 57..752

(xi) SEQUENCE DESCRIPTION: SEQ ID NO: 1:

```
GTCGACTGGA ACGAGACGAC CTGCTCTGTC ACAGGCATGA GGGGTCCCCG GCAGAG          56

ATG ACA GTG CTG GCG CCA GCC TGG AGC CCA AAT TCC TCC CTG TTG CTG       104
Met Thr Val Leu Ala Pro Ala Trp Ser Pro Asn Ser Ser Leu Leu Leu
1               5                  10                  15

CTG TTG CTG CTG CTG AGT CCT TGC CTG CGG GGG ACA CCT GAC TGT TAC       152
Leu Leu Leu Leu Leu Ser Pro Cys Leu Arg Gly Thr Pro Asp Cys Tyr
                20                  25                  30

TTC AGC CAC AGT CCC ATC TCC TCC AAC TTC AAA GTG AAG TTT AGA GAG       200
Phe Ser His Ser Pro Ile Ser Ser Asn Phe Lys Val Lys Phe Arg Glu
            35                  40                  45

TTG ACT GAC CAC CTG CTT AAA GAT TAC CCA GTC ACT GTG GCC GTC AAT       248
Leu Thr Asp His Leu Leu Lys Asp Tyr Pro Val Thr Val Ala Val Asn
        50                  55                  60

CTT CAG GAC GAG AAG CAC TGC AAG GCC TTG TGG AGC CTC TTC CTA GCC       296
Leu Gln Asp Glu Lys His Cys Lys Ala Leu Trp Ser Leu Phe Leu Ala
65                  70                  75                  80

CAG CGC TGG ATA GAG CAA CTG AAG ACT GTG GCA GGG TCT AAG ATG CAA       344
Gln Arg Trp Ile Glu Gln Leu Lys Thr Val Ala Gly Ser Lys Met Gln
                85                  90                  95

ACG CTT CTG GAG GAC GTC AAC ACC GAG ATA CAT TTT GTC ACC TCA TGT       392
Thr Leu Leu Glu Asp Val Asn Thr Glu Ile His Phe Val Thr Ser Cys
            100                 105                 110

ACC TTC CAG CCC CTA CCA GAA TGT CTG CGA TTC GTC CAG ACC AAC ATC       440
```

-continued

```
Thr Phe Gln Pro Leu Pro Glu Cys Leu Arg Phe Val Gln Thr Asn Ile
        115                 120                 125

TCC CAC CTC CTG AAG GAC ACC TGC ACA CAG CTG CTT GCT CTG AAG CCC      488
Ser His Leu Leu Lys Asp Thr Cys Thr Gln Leu Leu Ala Leu Lys Pro
    130                 135                 140

TGT ATC GGG AAG GCC TGC CAG AAT TTC TCT CGG TGC CTG GAG GTG CAG      536
Cys Ile Gly Lys Ala Cys Gln Asn Phe Ser Arg Cys Leu Glu Val Gln
145                 150                 155                 160

TGC CAG CCG GAC TCC TCC ACC CTG CTG CCC CCA AGG AGT CCC ATA GCC      584
Cys Gln Pro Asp Ser Ser Thr Leu Leu Pro Pro Arg Ser Pro Ile Ala
                165                 170                 175

CTA GAA GCC ACG GAG CTC CCA GAG CCT CGG CCC AGG CAG CTG TTG CTC      632
Leu Glu Ala Thr Glu Leu Pro Glu Pro Arg Pro Arg Gln Leu Leu Leu
            180                 185                 190

CTG CTG CTG CTG CTG CCT CTC ACA CTG GTG CTG CTG GCA GCC GCC TGG      680
Leu Leu Leu Leu Leu Pro Leu Thr Leu Val Leu Leu Ala Ala Ala Trp
        195                 200                 205

GGC CTT CGC TGG CAA AGG GCA AGA AGG AGG GGG GAG CTC CAC CCT GGG      728
Gly Leu Arg Trp Gln Arg Ala Arg Arg Arg Gly Glu Leu His Pro Gly
    210                 215                 220

GTG CCC CTC CCC TCC CAT CCC TAGGATTCGA GCCTTGTGCA TCGTTGACTC         779
Val Pro Leu Pro Ser His Pro
225                 230

AGCCAGGGTC TTATCTCGGT TACACCTGTA ATCTCAGCCC TTGGGAGCCC AGAGCAGGAT    839

TGCTGAATGG TCTGGAGCAG GTCGTCTCGT TCCAGTCGAC                          879

(2) INFORMATION FOR SEQ ID NO: 2:

(i) SEQUENCE CHARACTERISTICS:
        (A) LENGTH: 231 amino acids
        (B) TYPE: amino acid
        (D) TOPOLOGY: linear (ii) MOLECULE TYPE: protein (xi) SEQUENCE DESCRIPTION: SEQ ID NO: 2:

Met Thr Val Leu Ala Pro Ala Trp Ser Pro Asn Ser Ser Leu Leu Leu
1               5                   10                  15

Leu Leu Leu Leu Leu Ser Pro Cys Leu Arg Gly Thr Pro Asp Cys Tyr
            20                  25                  30

Phe Ser His Ser Pro Ile Ser Ser Asn Phe Lys Val Lys Phe Arg Glu
        35                  40                  45

Leu Thr Asp His Leu Leu Lys Asp Tyr Pro Val Thr Val Ala Val Asn
    50                  55                  60

Leu Gln Asp Glu Lys His Cys Lys Ala Leu Trp Ser Leu Phe Leu Ala
65                  70                  75                  80

Gln Arg Trp Ile Glu Gln Leu Lys Thr Val Ala Gly Ser Lys Met Gln
            85                  90                  95

Thr Leu Leu Glu Asp Val Asn Thr Glu Ile His Phe Val Thr Ser Cys
        100                 105                 110

Thr Phe Gln Pro Leu Pro Glu Cys Leu Arg Phe Val Gln Thr Asn Ile
    115                 120                 125

Ser His Leu Leu Lys Asp Thr Cys Thr Gln Leu Leu Ala Leu Lys Pro
130                 135                 140

Cys Ile Gly Lys Ala Cys Gln Asn Phe Ser Arg Cys Leu Glu Val Gln
145                 150                 155                 160

Cys Gln Pro Asp Ser Ser Thr Leu Leu Pro Pro Arg Ser Pro Ile Ala
                165                 170                 175
```

```
Leu Glu Ala Thr Glu Leu Pro Glu Pro Arg Pro Arg Gln Leu Leu Leu
            180                 185                 190
Leu Leu Leu Leu Leu Pro Leu Thr Leu Val Leu Leu Ala Ala Ala Trp
        195                 200                 205
Gly Leu Arg Trp Gln Arg Ala Arg Arg Arg Gly Glu Leu His Pro Gly
    210                 215                 220
Val Pro Leu Pro Ser His Pro
225                 230
```

(2) INFORMATION FOR SEQ ID NO: 3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO: 3:

```
TCGACTGGAA CGAGACGACC TGCT                                    24
```

(2) INFORMATION FOR SEQ ID NO: 4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO: 4:

```
AGCAGGTCGT CTCGTTCCAG                                         20
```

(2) INFORMATION FOR SEQ ID NO: 5:

(i) SEQUENCE CHARACTERISTICS:
        (A) LENGTH: 988 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (ix) FEATURE:
        (A) NAME/KEY: CDS
        (B) LOCATION: 30..734

(xi) SEQUENCE DESCRIPTION: SEQ ID NO: 5:

```
CGGCCGGAAT TCCGGGGCCC CCGGCCGAA ATG ACA GTG CTG GCG CCA GCC TGG    53
                                Met Thr Val Leu Ala Pro Ala Trp
                                  1               5

AGC CCA ACA ACC TAT CTC CTC CTG CTG CTG CTG AGC TCG GGA CTC       101
Ser Pro Thr Thr Tyr Leu Leu Leu Leu Leu Leu Ser Ser Gly Leu
     10                  15                  20

AGT GGG ACC CAG GAC TGC TCC TTC CAA CAC AGC CCC ATC TCC TCC GAC   149
Ser Gly Thr Gln Asp Cys Ser Phe Gln His Ser Pro Ile Ser Ser Asp
 25                  30                  35                  40
```

| | |
|---|---|
| TTC GCT GTC AAA ATC CGT GAG CTG TCT GAC TAC CTG CTT CAA GAT TAC<br>Phe Ala Val Lys Ile Arg Glu Leu Ser Asp Tyr Leu Leu Gln Asp Tyr<br>                45                   50                 55 | 197 |
| CCA GTC ACC GTG GCC TCC AAC CTG CAG GAC GAG GAG CTC TGC GGG GGC<br>Pro Val Thr Val Ala Ser Asn Leu Gln Asp Glu Glu Leu Cys Gly Gly<br>                60                   65                 70 | 245 |
| CTC TGG CGG CTG GTC CTG GCA CAG CGC TGG ATG GAG CGG CTC AAG ACT<br>Leu Trp Arg Leu Val Leu Ala Gln Arg Trp Met Glu Arg Leu Lys Thr<br>       75                 80                   85 | 293 |
| GTC GCT GGG TCC AAG ATG CAA GGC TTG CTG GAG CGC GTG AAC ACG GAG<br>Val Ala Gly Ser Lys Met Gln Gly Leu Leu Glu Arg Val Asn Thr Glu<br>                90                   95              100 | 341 |
| ATA CAC TTT GTC ACC AAA TGT GCC TTT CAG CCC CCC CCC AGC TGT CTT<br>Ile His Phe Val Thr Lys Cys Ala Phe Gln Pro Pro Pro Ser Cys Leu<br>105                 110                  115               120 | 389 |
| CGC TTC GTC CAG ACC AAC ATC TCC CGC CTC CTG CAG GAG ACC TCC GAG<br>Arg Phe Val Gln Thr Asn Ile Ser Arg Leu Leu Gln Glu Thr Ser Glu<br>                     125                  130               135 | 437 |
| CAG CTG GTG GCG CTG AAG CCC TGG ATC ACT CGC CAG AAC TTC TCC CGG<br>Gln Leu Val Ala Leu Lys Pro Trp Ile Thr Arg Gln Asn Phe Ser Arg<br>                140                  145               150 | 485 |
| TGC CTG GAG CTG CAG TGT CAG CCC GAC TCC TCA ACC CTG CCA CCC CCA<br>Cys Leu Glu Leu Gln Cys Gln Pro Asp Ser Ser Thr Leu Pro Pro Pro<br>          155                  160               165 | 533 |
| TGG AGT CCC CGG CCC CTG GAG GCC ACA GCC CCG ACA GCC CCG CAG CCC<br>Trp Ser Pro Arg Pro Leu Glu Ala Thr Ala Pro Thr Ala Pro Gln Pro<br>       170                175               180 | 581 |
| CCT CTG CTC CTC CTA CTG CTG CTG CCC GTG GGC CTC CTG CTG CTG GCC<br>Pro Leu Leu Leu Leu Leu Leu Leu Pro Val Gly Leu Leu Leu Leu Ala<br>185                 190                  195               200 | 629 |
| GCT GCC TGG TGC CTG CAC TGG CAG AGG ACG CGG CGG AGG ACA CCC CGC<br>Ala Ala Trp Cys Leu His Trp Gln Arg Thr Arg Arg Arg Thr Pro Arg<br>                   205                 210               215 | 677 |
| CCT GGG GAG CAG GTG CCC CCC GTC CCC AGT CCC CAG GAC CTG CTG CTT<br>Pro Gly Glu Gln Val Pro Pro Val Pro Ser Pro Gln Asp Leu Leu Leu<br>                220                  225               230 | 725 |
| GTG GAG CAC TGACCTGGCC AAGGCCTCAT CCTGCGGAGC CTTAAACAAC<br>Val Glu His<br>              235 | 774 |
| GCAGTGAGAC AGACATCTAT CATCCCATTT TACAGGGGAG GATACTGAGG CACACAGAGG | 834 |
| GGAGTCACCA GCCAGAGGAT GTATAGCCTG GACACAGAGG AAGTTGGCTA GAGGCCGGTC | 894 |
| CCTTCCTTGG GCCCCTCTCA TTCCCTCCCC AGAATGGAGG CAACGCCAGA ATCCAGCACC | 954 |
| GGCCCCATTT ACCCAACTCT GAACAAAGCC CCCG | 988 |

(2) INFORMATION FOR SEQ ID NO: 6:

(i) SEQUENCE CHARACTERISTICS:
        (A) LENGTH: 235 amino acids
        (B) TYPE: amino acid
        (D) TOPOLOGY: linear (ii) MOLECULE TYPE: protein (xi) SEQUENCE DESCRIPTION: SEQ ID NO: 6:

Met Thr Val Leu Ala Pro Ala Trp Ser Pro Thr Thr Tyr Leu Leu Leu
  1             5                   10                 15

Leu Leu Leu Leu Ser Ser Gly Leu Ser Gly Thr Gln Asp Cys Ser Phe
              20                   25                 30

Gln His Ser Pro Ile Ser Ser Asp Phe Ala Val Lys Ile Arg Glu Leu

```
                35                  40                  45
Ser Asp Tyr Leu Leu Gln Asp Tyr Pro Val Thr Val Ala Ser Asn Leu
 50                  55                  60

Gln Asp Glu Glu Leu Cys Gly Gly Leu Trp Arg Leu Val Leu Ala Gln
 65                  70                  75                  80

Arg Trp Met Glu Arg Leu Lys Thr Val Ala Gly Ser Lys Met Gln Gly
                 85                  90                  95

Leu Leu Glu Arg Val Asn Thr Glu Ile His Phe Val Thr Lys Cys Ala
                100                 105                 110

Phe Gln Pro Pro Pro Ser Cys Leu Arg Phe Val Gln Thr Asn Ile Ser
            115                 120                 125

Arg Leu Leu Gln Glu Thr Ser Glu Gln Leu Val Ala Leu Lys Pro Trp
        130                 135                 140

Ile Thr Arg Gln Asn Phe Ser Arg Cys Leu Glu Leu Gln Cys Gln Pro
145                 150                 155                 160

Asp Ser Ser Thr Leu Pro Pro Pro Trp Ser Pro Arg Pro Leu Glu Ala
                165                 170                 175

Thr Ala Pro Thr Ala Pro Gln Pro Pro Leu Leu Leu Leu Leu Leu Leu
                180                 185                 190

Pro Val Gly Leu Leu Leu Leu Ala Ala Ala Trp Cys Leu His Trp Gln
            195                 200                 205

Arg Thr Arg Arg Arg Thr Pro Arg Pro Gly Glu Gln Val Pro Pro Val
        210                 215                 220

Pro Ser Pro Gln Asp Leu Leu Leu Val Glu His
225                 230                 235

(2) INFORMATION FOR SEQ ID NO: 7:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO: 7:

AATTGGTACC TTTGGATAAA AGAGACTACA AGGACGACGA TGACAAGACA CCTGACTGTT        60

ACTTCAGCCA C                                                            71

(2) INFORMATION FOR SEQ ID NO: 8:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO: 8:

ATATGGATCC CTACTGCCTG GGCCGAGGCT CTGGGAG                                 37
```